United States Patent
Chandrakumar et al.

(10) Patent No.: US 11,025,215 B2
(45) Date of Patent: Jun. 1, 2021

(54) HIGH INPUT IMPEDANCE, HIGH DYNAMIC RANGE, COMMON-MODE-INTERFERER TOLERANT SENSING FRONT-END FOR NEUROMODULATION SYSTEMS

(71) Applicant: The Regents of the University of California, Oakland, CA (US)

(72) Inventors: Hariprasad Chandrakumar, Los Angeles, CA (US); Dejan Markovic, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 22 days.

(21) Appl. No.: 16/467,456

(22) PCT Filed: Dec. 7, 2017

(86) PCT No.: PCT/US2017/065039
§ 371 (c)(1),
(2) Date: Jun. 6, 2019

(87) PCT Pub. No.: WO2018/106877
PCT Pub. Date: Jun. 14, 2018

(65) Prior Publication Data
US 2020/0099352 A1      Mar. 26, 2020

Related U.S. Application Data

(60) Provisional application No. 62/431,420, filed on Dec. 7, 2016.

(51) Int. Cl.
*H03F 1/02*     (2006.01)
*H03F 3/45*     (2006.01)
(Continued)

(52) U.S. Cl.
CPC .......... *H03F 3/45475* (2013.01); *A61B 5/24* (2021.01); *A61B 5/7217* (2013.01); *A61M 21/00* (2013.01);
(Continued)

(58) Field of Classification Search
CPC ............... H03F 1/02; H03F 3/005; H03F 3/45
(Continued)

(56) References Cited

U.S. PATENT DOCUMENTS

| 5,633,989 A | 5/1997 | Shin et al. |
| 5,847,601 A | 12/1998 | Wang |

(Continued)

FOREIGN PATENT DOCUMENTS

| EP | 3202033 A1 | 8/2017 |
| JP | H06197877 A | 7/1994 |

(Continued)

OTHER PUBLICATIONS

Extended European Search Report for European Application No. 15847435.3, Search completed Apr. 20, 2018, dated Jan. 30, 2019, 11 Pgs.

(Continued)

*Primary Examiner* — Steven J Mottola
(74) *Attorney, Agent, or Firm* — KPPB LLP

(57) ABSTRACT

Neuromodulation systems in accordance with embodiments of the invention can use a feed-forward common-mode cancellation (CMC) path to attenuate common-mode (CM) artifacts appearing at a voltage input, thus allowing for the simultaneous recording of neural data and stimulation of neurons. In several embodiments of the invention, the feed-forward CMC path is utilized to attenuate the common-mode swings at $V_{in,CM}$, which can restore the linear operation of the front-end for differential signals. In several embodiments, the neuromodulation system may utilize an (Continued)

anti-alias filter (AAF) that includes a duty-cycles resistor (DCR) switching at a first frequency $f_1$, followed by a DCR switching at a second frequency $f_2$. The AAF allows for a significantly reduced second frequency $f_2$ that enables the multi-rate DCR to increase the maximum realizable resistance, which is dependent upon the frequency ratio $f_1/f_2$.

14 Claims, 48 Drawing Sheets

(51) Int. Cl.
| | | |
|---|---|---|
| *A61B 5/00* | (2006.01) | |
| *A61M 21/00* | (2006.01) | |
| *H03F 1/26* | (2006.01) | |
| *H03F 1/56* | (2006.01) | |
| *A61B 5/24* | (2021.01) | |

(52) U.S. Cl.
CPC ............... *H03F 1/26* (2013.01); *H03F 1/56* (2013.01); *H03F 2200/261* (2013.01); *H03F 2200/459* (2013.01); *H03F 2203/45138* (2013.01)

(58) Field of Classification Search
USPC ..................................... 330/9, 258; 327/124
See application file for complete search history.

(56) References Cited

U.S. PATENT DOCUMENTS

| | | |
|---|---|---|
| 6,456,159 B1 | 9/2002 | Brewer |
| 7,132,883 B2 | 11/2006 | Huijsing et al. |
| 7,696,817 B1 | 4/2010 | Boucher et al. |
| 7,724,080 B2 | 5/2010 | Luff |
| 8,786,363 B2 | 7/2014 | Ahmad |
| 9,912,309 B1 | 3/2018 | Ecker et al. |
| 10,003,306 B1 | 6/2018 | Larson et al. |
| 2006/0189881 A1 | 8/2006 | Fassio |
| 2008/0106330 A1 | 5/2008 | Yoshida et al. |
| 2008/0269631 A1 | 10/2008 | Denison et al. |
| 2009/0082829 A1 | 3/2009 | Panken et al. |
| 2009/0309653 A1 | 12/2009 | Luff |
| 2010/0033240 A1 | 2/2010 | Denison et al. |
| 2012/0188009 A1 | 7/2012 | Alexander et al. |
| 2013/0303942 A1 | 11/2013 | Damaser et al. |
| 2013/0335141 A1 | 12/2013 | Ahmad |
| 2015/0357979 A1* | 12/2015 | Ouchi ............... H03F 3/393 330/9 |
| 2016/0294331 A1 | 10/2016 | Ivanov |
| 2017/0230019 A1 | 8/2017 | Chandrakumar et al. |

FOREIGN PATENT DOCUMENTS

| | | |
|---|---|---|
| WO | 2014087980 A1 | 6/2014 |
| WO | 2016054274 A1 | 4/2016 |
| WO | 2018106877 A1 | 6/2018 |

OTHER PUBLICATIONS

International Preliminary Report on Patentability for International Application PCT/US2015/053336, dated Apr. 4, 2017, dated Apr. 13, 2017, 6 Pgs.
International Preliminary Report on Patentability for International Application PCT/US2017/065039, dated Jun. 11, 2019, dated Jun. 20, 2019, 5 Pgs.
International Search Report and Written Opinion for International Application No. PCT/US2015/053336, Search completed Jan. 13, 2016, dated Jan. 13, 2016, 8 Pgs.
International Search Report and Written Opinion for International Application No. PCT/US2017/065039, Search completed Feb. 12, 2018, dated Mar. 6, 2018, 14 Pgs.
Partial Supplementary European Search Report for European Application No. 15847435.3, Search completed Apr. 20, 2018, dated Oct. 26, 2018, 13 Pgs.
Ahmed et al., "A low-power Gm-C-based CT-ΔΣ audio-band ADC in 1.1V 65nm CMOS", IEEE VLSI, Jun. 19, 2015, pp. C294-C295.
Akita et al., "A 0.06mm2 14nV/√Hz chopper instrumentation amplifier with automatic differential-pair matching", Solid-State Circuits (ISSCC), IEEE International Conference, Feb. 17-21, 2013, San Francisco, CA, USA, pp. 178-179, DOI: 10.1109/ISSCC.2013.6487689.
Basir-Kazeruni et al., "A blind Adaptive Stimulation Artifact Rejection (ASAR) engine for closed-loop implantable neuromodulation systems", Proceedings of the 8th International IEEE/EMBS Conference on Neural Engineering (NER), Shanghai, China, May 25-28, 2017, 4 pgs.
Belloni et al., "Low-Power Ripple-Free Chopper Amplifier with Correlated Double Sampling De-Chopping", IEEE International Symposium on Circuits and Systems (ISCAS), May 30-Jun. 2, 2010, Paris, France, pp. 765-768, DOI: 10.1109/ISCAS.2010.5537462.
Benabid et al., "Deep brain stimulation of the subthalamic nucleus for the treatment of Parkinson's disease", The Lancet Neurology, vol. 8, No. 1, Jan. 1, 2009, pp. 67-81.
Borghi et al., "A power-efficient analog integrated circuit for amplification and detection of neural signals", Engineering in Medicine and Biology Society (EMBC), Annual International Conference of the IEEE, Aug. 20-25, 2008, Vancouver, BC, Canada, pp. 4911-4915, DOI: 10.1109/IEMBS.2008.4650315.
Burt et al., "A Micropower Chopper-Stabilized Operational Amplifier Using a SC Notch Filter Wth Synchronous Integration Inside the Continuous-Time Signal Path", IEEE Journal of Solid-State Circuits, Dec. 2006, First Published: Nov. 20, 2006, vol. 41, No. 12, pp. 2729-2736, DOI: 10.1109/JSSC.2006.884195.
Chandrakumar et al., "A 2μW 40mVpp linear-input-range chopper-stabilized bio-signal amplifier with boosted input impedance of 300MΩ and electrode-offset filtering", Solid-State Circuits (ISSCC), IEEE International Conference, Jan. 31 to Feb. 4, 2016, San Francisco, CA, USA, pp. 96-97, DOI: 10.1109/ISSCC.2016.7417924.
Chandrakumar et al., "A High Dynamic-Range Neural Recording Chopper Amplifier for Simultaneous Neural Recording and Stimulation", IEEE Journal of Solid-State Circuits, vol. 52, No. 3, Mar. 2017, First Published: Jan. 27, 2017, pp. 645-656, DOI: 10.1109/JSSC.2016.2645611.
Denison et al., "A 2 μw, 100 nV/rtHz Chopper-Stabilized Instrumentation Amplifier for Chronic Measurement of Neural Field Potentials", in IEEE Journal of Solid-State Circuits, Dec. 1, 2007, vol. 42, No. 12, pp. 2934-2945.
Engel et al., "Invasive Recordings from the Human Brain: Clinical Insights and Beyond", Nature Reviews Neuroscience, vol. 6, No. 1, Jan. 2005, pp. 35-47.
Enz et al., "Circuit techniques for reducing the effects of op-amp imperfections: autozeroing, correlated double sampling, and chopper stabilization", Proceedings of the IEEE, Nov. 1996, vol. 84, No. 11, pp. 1584-1614, DOI: 10.1109/5.542410.
Fan et al., "A 1.8 μW 32 nV/√Hz Capacitively-Coupled Chopper Instrumentation Amplifier in 65 nm CMOS for Wireless Sensor Nodes", IEEE JSSC, Jul. 2011, vol. 46, No. 7, pp. 1534-1543.
Gonen et al., "A Dynamic Zoom ADC With 109-dB DR for Audio Applications", IEEE JSSC, Jun. 2017, vol. 52, No. 6, pp. 1542-1550.
Greenwald et al., "A Bidirectional Neural Interface IC With Chopper Stabilized BioADC Array and Charge Balanced Stimulator", IEEE Transactions on Biomedical Circuits and Systems, vol. 10, No. 5, Oct. 2016, pp. 990-1002.
Gubellini et al., "Deep brain stimulation in neurological diseases and experimental models: From molecule to complex behavior", Prog. Neurobiol. Sep. 2009, vol. 89, No. 1, pp. 79-123.
Harpe et al., "A 26μW 8 bit 10 MS/s Asynchronous SAR ADC for Low Energy Radios", IEEE Journal of Solid-State Circuits, vol. 46, No. 7, Jul. 2011, pp. 1585-1595.

(56) References Cited

OTHER PUBLICATIONS

Harrison et al., "A Low-Power Integrated Circuit for a Wireless 100-Electrode Neural Recording System", IEEE Journal of Solid-State Circuits, vol. 42, No. 1, Jan. 2007, pp. 123-133.
Harrison et al., "A Low-Power Low-Noise CMOS Amplifier for Neural Recording Applications", IEEE Journal of Solid-State Circuits, vol. 38, No. 6, Jun. 2003, pp. 958-965.
Hochberg et al., "Neuronal ensemble control of prosthetic devices by a human with tetraplegia", Nature, vol. 442, No. 7099, Jul. 13, 2006, pp. 164-171.
Islam, "Artifact Characterization, Detection and Removal from Neural Signals", National University of Singapore, PhD Thesis, 2015, 275 pgs., (presented in 2 parts).
Jiang et al., "A 4.5 nV/√Hz Capacitively Coupled Continuous-Time Sigma-Delta Modulator with an Energy-Efficient Chopping Scheme", IEEE Solid-State Circuits Letters, vol. 1, No. 1, Jan. 2018, pp. 18-21.
Jochum et al., "Integrated circuit amplifiers for multi-electrode intracortical recording", Journal of Neural Engineering, vol. 6, No. 1, Feb. 2009, Electronic Publication: Jan. 12, 2009, pp. 1-26.
Johnson et al., "An implantable 700μW 64-channel neuromodulation IC for simultaneous recording and stimulation with rapid artifact recovery", IEEE VLSI, Jun. 2017, pp. C48-C49.
Kisban et al., "Microprobe Array with Low Impedance Electrodes and Highly Flexible Polyimide Cables for Acute Neural Recording", Proceedings of the 29th Annual International Conference of the IEEE Engineering in Medicine and Biology Society, Lyon, France, Aug. 22-26, 2007, pp. 175-178.
Kusuda, "Auto Correction Feedback for Ripple Suppression in a Chopper Amplifier", IEEE Journal of Solid-State Circuits, Aug. 2010, First Published: Jul. 23, 2010, vol. 45, No. 8, pp. 1436-1445, DOI: 10.1109/JSSC.2010.2048142.
Liu et al., "A 1V 11fJ/conversion-step 10bit 10MS/s asynchronous SAR ADC in 0.18μm CMOS", Proceedings of 2010 Symposium on VLSI Circuits, Honolulu, Hawaii, Jun. 16-18, 2010, 2 pgs.
Liu et al., "Design of a Closed-Loop, Bidirectional Brain Machine Interface System Wth Energy Efficient Neural Feature Extraction and PID Control", IEEE Transactions on Biomedical Circuits and Systems, vol. 11, No. 4, Aug. 2017, pp. 729-742.
Majidzadeh et al., "Energy Efficient Low-Noise Neural Recording Amplifier With Enhanced Noise Efficiency Factor", IEEE Transactions on Biomedical Circuits and Systems, vol. 5, No. 3, Jun. 2011, pp. 262-271.
Muller et al., "A 0.013 mm2, 5 μw, DC-Coupled Neural Signal Acquisition IC with 0.5 V Supply", IEEE JSSC, Jan. 2012, vol. 47, No. 1, pp. 232-243.
Muller et al., "A miniaturized 64-channel 225μW wireless electrocorticographic neural sensor", IEEE ISSCC, Feb. 2014, pp. 412-413.
Omran et al., "Matching Properties of Femtofarad and Sub-Femtofarad MOM Capacitors", IEEE Transactions on Circuits and Systems—I: Regular Papers, vol. 63, No. 6, Jun. 2016, pp. 763-772.
Parastarfeizabadi et al., "Advances in closed-loop deep brain stimulation devices", Journal of NeuroEngineering and Rehabilitation, vol. 14, No. 79, Aug. 11, 2017, 20 pgs.
Pavan et al., "A Power Optimized Continuous-Time ΔΣ ADC for Audio Applications", IEEE JSSC, Feb. 2008, vol. 43, No. 2, pp. 351-360.
Rutishauser et al., "Human memory strength is predicted by theta-frequency phase-locking of single neurons", Nature Letters, Apr. 8, 2010, vol. 464, pp. 903-907.
Schwartz et al., "Brain Controlled Interfaces: Movement Restoration with Nerual Prosthetics", Neuron, Oct. 5, 2006, vol. 52, pp. 205-220.
Suthana et al., "Memory Enhancement and Deep-Brain Stimulation of the Entorhinal Area", The New England Journal of Medicine, Feb. 9, 2012, vol. 366, pp. 502-510.
Truccolo et al., "Single-neuron dynamics in human focal epilepsy", Nature Neuroscience, vol. 14, Mar. 27, 2011, pp. 635-641.
Van Elzakker et al., "A 10-bit Charge-Redistribution ADC Consuming 1.9 μW at 1 MS/s", IEEE JSSC, 2010, vol. 45, No. 5, pp. 1007-1015.
Wattanapanitch et al., "An Energy-Efficient Micropower Neural Recording Amplifier", IEEE Transactions on Biomedical Circuits and Systems, vol. 1, No. 2, Jun. 2007, pp. 136-147.
Wolf, "Thermal Considerations for the Design of an Implanted Cortical Brain-Machine Interface (BMI)", Chapter 3 of "Indwelling Neural Implants: Strategies for Contending with the In Vivo Environment", 2008, Retrieved From: https://www.ncbi.nlm.nih.gov/books/NBK3932, 20 pgs.
Wu et al., "A Chopper Current-Feedback Instrumentation Amplifier With a 1 mHz 1/f Noise Corner and an AC-Coupled Ripple Reduction Loop", IEEE Journal of Solid-State Circuits, Dec. 15, 2009, vol. 44, No. 12, pp. 3232-3243, DOI: 10.1109/JSSC.2009.2032710.
Xu et al., "A 160 μW 8-Channel Active Electrode System for EEG Monitoring", IEEE Transactions on Biomedical Circuits and Systems, Dec. 2011, First Published: Nov. 11, 2011, vol. 5, No. 6, pp. 555-567, DOI: 10.1109/TBCAS.2011.2170985.
Zhang et al., "Design of Ultra-Low Power Biopotential Amplifiers for Biosignal Acquisition Applications", IEEE Transactions on Biomedical Circuits and Systems, vol. 6, No. 4, Aug. 2012, pp. 344-355.
Billa et al., "A 280μW 24kHz-BW 98.5dB-SNDR chopped single-bit CT ΔΣm achieving <10Hz 1/f noise corner without chopping artifacts", 2016 IEEE International Solid-State Circuits (ISSCC), San Francisco, CA, 2016, pp. 276-277.
Billa et al., "Analysis and Design of Continuous-Time Delta-Sigma Converters Incorporating Chopping", IEEE JSSC, Sep. 2017, vol. 52, No. 9, pp. 2350-2361.
Chandrakumar et al., "A 15.2-enob continuous-time ΔΣadc for a 7.3 μW 200mvpp-linear-input-range neural recording front-end", Proceedings of IEEE International Solid-State Circuits Conference (ISSCC), San Francisco, California, Feb. 11-15, 2018.
Chandrakumar et al., "A 2.8μW 80mVpp-linear-input-range 1.6GΩ-input impedance bio-signal chopper amplifier tolerant to common-mode interference up to 650mVpp", IEEE ISSCC, 2017, pp. 448-449.
Chandrakumar et al., "An 80-mVpp Linear-Input Range, 1.6-GΩ Input Impedance, Low-Power Chopper Amplifier for Closed-Loop Neural Recording That Is Tolerant to 650-mVpp Common-Mode Interference", IEEE Journal of Solid-State Circuits, vol. 52, No. 11, Nov. 2017, pp. 2811-2828.
De Berti et al., "A 106 dB A-Weighted DR Low-Power Continuous-Time ΣΔ Modulator for MEMS Microphones", IEEE Journal of Solid-State Circuits, vol. 51, No. 7, Jul. 2016, pp. 1607-1618.
De La Rosa et al., "Next-Generation Delta-Sigma Converters: Trends and Perspectives", IEEE Journal on Emerging and Selected Topics in Circuits and Systems, vol. 5, No. 4, Dec. 2015, pp. 484-499.
Jiang et al., "A ±50-mV Linear-Input-Range VCO-Based Neural-Recording Frong-End with Digital Nonlinearity Correction", IEEE JSSC, Jan. 2017, vol. 52, pp. 173-184.
Karkare et al., "Robust, reconfigurable, and power-efficient biosignal recording systems", Proceedings of the IEEE 2014 Custom Integrated Circuits Conference, San Jose, California, Sep. 15-17, 2014.
Kim et al., "A 92dB dynamic range sub-μVrms-noise 0.8μpW/ch neural-recording ADC array with predictive digital autoranging", Proceedings of IEEE International Solid-State Circuits Conference (ISSCC), San Francisco, California, Feb. 11-15, 2018.
Leow et al., "A 1 V 103 dB 3rd-Order Audio Continuous-Time ΔΣ ADC Wth Enhanced Noise Shaping in 65 nm CMOS", IEEE Journal of Solid-State Circuits, vol. 51, No. 11, Nov. 2016, pp. 2625-2638.
Murmann, "The Race for the Extra Decibel: A Brief Review of Current ADC Performance Trajectories", IEEE Solid-State Circuits Magazine, vol. 7, No. 3, Sep. 2015, pp. 58-66.
Najafi, "Solid-state microsensors for cortical nerve recordings", IEEE Engineering in Medicine and Biology Magazine, vol. 13, No. 3, Jun.-Jul. 1994, pp. 375-387.

(56) References Cited

OTHER PUBLICATIONS

Ng et al., "A Low-Power, High CMRR Neural Amplifier System Employing CMOS Inverter-Based OTAs With CMFB Through Supply Rails", IEEE Journal of Solid-State Circuits, vol. 51, No. 3, Mar. 2016, pp. 724-737.
Rozgic et al., "A true full-duplex 32-channel 0.135cm3 neural interface", Proceedings of IEEE Biomedical Circuits and Systems Conference (BioCAS), Turin, Italy, Oct. 19-21, 2017, 4 pgs.
Stanslaski et al., "Design and Validation of a Fully Implantable, Chronic, Closed-Loop Neuromodulation Device Wth Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Sukumaran et al., "Low Power Design Techniques for Single-Bit Audio Continuous-Time Delta Sigma ADCs Using FIR Feedback", IEEE Journal of Solid-State Circuits, vol. 49, No. 11, Nov. 2014, pp. 2515-2525.
Wang et al., "A 0.022 mm2 98.5 dB SNDR Hybrid Audio ΔΣ Modulator With Digital ELD Compensation in 28 nm CMOS", IEEE Journal of Solid-State Circuits, vol. 50, No. 11, Nov. 2015, pp. 2655-2664.

\* cited by examiner

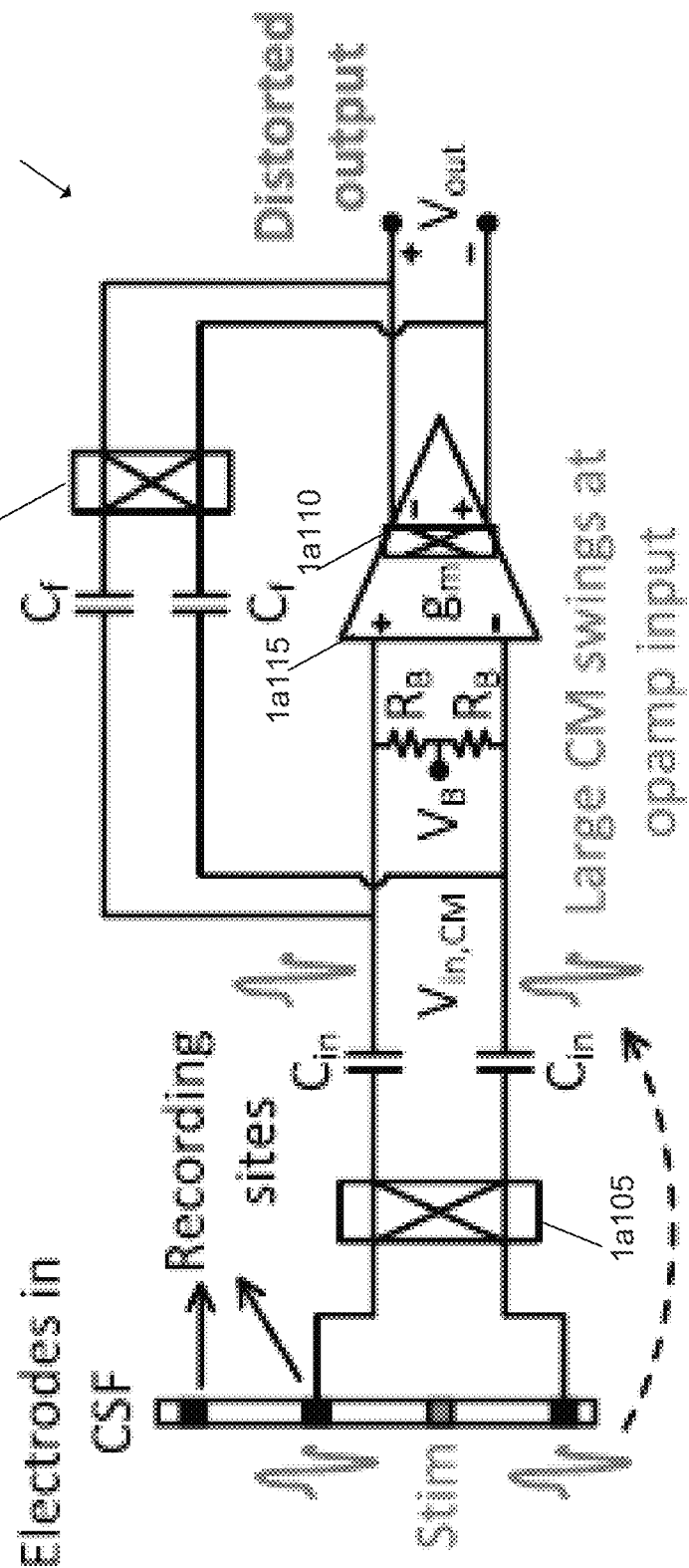
FIG. 1a - PRIOR ART

| Spec | [2] JSSC'07 | [3] JSSC'11 | [4] JSSC'12 | [5] ISSCC'14 | [6] ISSCC'16 | This work |
|---|---|---|---|---|---|---|
| Power/Ch | 2 μW | 1.8 μW | 5.04 μW | 2.3 μW | 2 μW | 2.8 μW |
| Supply | 1.8 V | 1 V | 0.5 V | 0.5 V | 1.2 V | 1.2 V |
| Signals[a] | LFP | LFP | AP + LFP | LFP | AP + LFP | AP + LFP |
| Peak Input | 5 mV$_p$ | — | — | 0.5 mV$_p$ | 20 mV$_p$ | 40 mV$_p$ |
| Input-referred noise ($V_{rms}$) | LFP: 1 μV | LFP: 6.7 μV | AP: 4.7 μV LFP: 4.3 μV | LFP: 1.3 μV | AP: 7 μV LFP: 2 μV | AP: 5.3 μV LFP: 1.8 μV |
| NEF | LFP: 4.6 | LFP: 14 | AP: 5.99 LFP: 30 | LFP: 4.76 | AP: 4.9 LFP: 7 | AP: 4.4 LFP: 7.4 |
| DC Input-impedance | 8 MΩ | 6 MΩ | ∞ | 28 MΩ | 300 MΩ | 1.6 GΩ |
| Off-chip caps | Yes | Yes | No | Yes | Yes | No |
| Dynamic Range[b] | 67 dB (LFP) | — | ~35 dB | 50 dB (LFP) | 69 dB (AP) 78 dB (LFP) | 74 dB (AP) 81 dB (LFP) |
| Total Harmonic Distortion | −60 dB | — | −37 dB | −48 dB | −74 dB | −76 dB |
| Tolerance to large-signal CM | No | No | No | No | No | Up to 650 mV$_{pp}$ |
| Area/ch | 1.7 mm² | 0.1 mm² | 0.013 mm² | 0.025 mm² | 0.071 mm² | 0.069 mm² |
| Technology | 0.8 um | 65 nm | 65 nm | 65 nm | 40 nm | 40 nm |

[a] LFP: Local Field Potentials, AP: Action Potentials
[b] Calculated for distortion power = noise power

FIG. 6

| Channel # | 1 | 2 | 3 | 4 | 5 | 6 | 7 | 8 | 9 | 10 | 11 | 12 |
|---|---|---|---|---|---|---|---|---|---|---|---|---|
| Measured offset at electrode $V_{el}$ (mV) with aux-chop disabled | 7.5 | 9.1 | 36 | 45 | 6.1 | 7.6 | 5.7 | 21.4 | 2.8 | 12.6 | 3.6 | 18 |

FIG. 9a

HIGH INPUT IMPEDANCE, HIGH DYNAMIC RANGE, COMMON-MODE-INTERFERER TOLERANT SENSING FRONT-END FOR NEUROMODULATION SYSTEMS

STATEMENT REGARDING FEDERALLY SPONSORED RESEARCH OR DEVELOPMENT

This invention was made with government support under Grant No. DARPA-BAA-14-08, awarded by the U.S. Department of Defense, Defense Advanced Research Projects Agency. They government has certain rights in the invention.

FIELD OF THE INVENTION

The present invention generally relates to amplifiers and more specifically to systems and methods for increasing input impedance, increasing tolerance to differential and common-mode interference, and ripple reduction in chopped bio-signal amplifiers.

CROSS REFERENCE TO RELATED APPLICATIONS

This application is a national stage of PCT Patent Application No. PCT/US2017/065039, entitled "A High Input Impedance, High Dynamic Range, Common-Mode-Interferer Tolerant Sensing Front-End For Neuromodulation Systems" to Chandrakumar et al., filed Dec. 7, 2017, which claims priority to U.S. Provisional Application No. 62/431,420, entitled "High Input Impedance, High Dynamic Range, Common-Mode-Interferer Tolerant Sensing Front-End for Neuromodulation Systems" to Chandrakumar et al., filed Dec. 7, 2016, the disclosures of which are incorporated by reference herein in their entirety.

BACKGROUND

There has been great interest in the neuroscience community in decoding the functioning of the brain. Among the various methods used, analysis of the recordings of the electrical activity of neurons has been among the most important tools available. These recordings can be indispensable for understanding and diagnosing neurological disorders like epileptic seizures, in the creation of brain-machine interfaces, and for neuro-prosthetic technologies to aid paralyzed patients. Further, modern neuroscience is attempting to "close the loop" with the brain, by stimulating specific areas using current pulses, and recording neuronal responses to learn and adapt the stimulation patterns. For example, it has been demonstrated in a limited number of patients that stimulating certain regions of the entorhinal cortex of the brain could improve memory function.

Typically, extracellular recordings of neural signals occupy a frequency band from 1 Hz to about 5 kHz, and have relatively small amplitudes, ranging from 1 $mV_p$ for Local Field Potentials (LFPs) to 100 $\mu V_p$ for Action Potentials (APs). Due to their small amplitudes, neural signals are often amplified before digitization. Where the peak input-signal amplitudes are on the order of 1 mV, the input-referred noise of an amplifier should be less than 4 $\mu V_{rms}$ for 8-bit resolution. Thus, low-noise bio-signal amplifiers could be utilized in various signal recording systems including (but not limited to) recording neural signals.

SUMMARY OF THE INVENTION

Common-mode-interferer tolerant sensing front-ends for neuromodulation systems in accordance with embodiments of the invention are discloses. In one embodiment, a chopper amplifier includes: a pair of inputs $V_{in,\,CM}$ configured to receive a differential input signal and a common-mode (CM) signal; an input capacitor $C_{in}$ connected in series with each of the pair of inputs $V_{in,\,CM}$ having capacitance $C_{in}$; an operational amplifier $g_m$; and a common-mode cancellation (CMC) path to attenuate common-mode (CM) swings at $V_{in,\,CM}$, including: an operational amplifier $g_{ma}$ with a gain $A_{cm}$ and capacitors $C_a$ and $C_b$ configured to sense and amplify an input CM signal; $C_{cm}$ capacitors configured to subtract the amplified CM signal from the input signal $V_{in,\,CM}$ received on each of the pair of inputs.

In a further embodiment, the $C_{cm}$ capacitors have capacitances that are the ratio of the capacitance of the input capacitors $C_{in}$ and the gain $A_{cm}$ of the operational amplifier.

In another embodiment, a gain in the CMC path is set by the capacitor ratio $A_{cm}=2\,C_a/C_b$.

In a still further embodiment, a $C_{cm}$ capacitor is sized to be $C_{in}/A_{cm}$.

In still another embodiment, capacitor $C_{in}$ and $C_{cm}$ are matching.

In a yet further embodiment, capacitor $C_{cm}$ is sized smaller than capacitor $C_{in}$ to minimize increase in input-referred noise.

In still another embodiment again, the chopper amplifier further includes power supply circuitry configured to integrate a charge-pump on-chip to generate a local voltage supply for the operational amplifier $g_{ma}$ in the CMC path from the available voltage supply.

In a still further embodiment again, bandwidth of the CMC path is greater than the bandwidth of the CM artifacts.

In a yet further embodiment again, the requirements of $g_{ma}$ are:

$$g_{ma}\left(\frac{C_b}{C_b+2C_a}\right)\frac{1}{2\pi(C_b+2C_{cm})} > 30\text{ kHz}$$

In a yet further additional embodiment, there is no chopping at an output of the CMC path such that the CM-to-DM single at the CMC output remains at baseband as compared to the up-modulated differential input signal.

In still another embodiment, the chopper amplifier further includes at least one feedback loop including a multi-rate duty-cycled resistor (MDCR), wherein the MDCR comprises a first anti-alias filter (AAF) comprising a duty-cycled resistor (DCR) formed by $R_1$ switching at $f_1$, and a capacitor $C_1$ followed by a second low-pass filter formed by a DCR $R_2$ switching at $f_2$, and a capacitor $C_2$, wherein the AAF allows for a significantly reduced switching frequency $f_2$, as the AAF reduces the bandwidth of the signal flowing into the second low-pass filter.

In yet another embodiment again, a lower limit on the switching frequency $f_2$ is determined by the bandwidth $f_{aaf}$ of the AAF and the required attenuation of the aliased components.

In still another embodiment, the chopper amplifier further includes an auxiliary path comprising two storage capacitors with capacitance $C_{aux}$ and switching circuitry configured using offset modulation to pre-charge the input capacitors $C_{in}$ during a pre-charging phase.

In a further additional embodiment, the chopper amplifier includes passive mixers $M_{1,2}$ in the auxiliary path, where a frequency of a ripple at electrodes is equal to the clock frequency $F_{aux}$ used in the mixers $M_{1,2}$.

BRIEF DESCRIPTION OF THE DRAWINGS

FIG. 1a is a schematic diagram illustrating a response of a conventional chopper amplifier to common mode inputs.

FIG. 1l illustrates a low-bandwidth integrator using an MDCR in accordance with an embodiment of the invention.

FIG. 6 illustrates a comparison an embodiment of the invention with the current state-of-the-art.

FIG. 9a illustrates large offsets observed at an electrode when aux-path chopping is disabled in accordance with an embodiment of the invention.

DETAILED DESCRIPTION

Figure 1B:
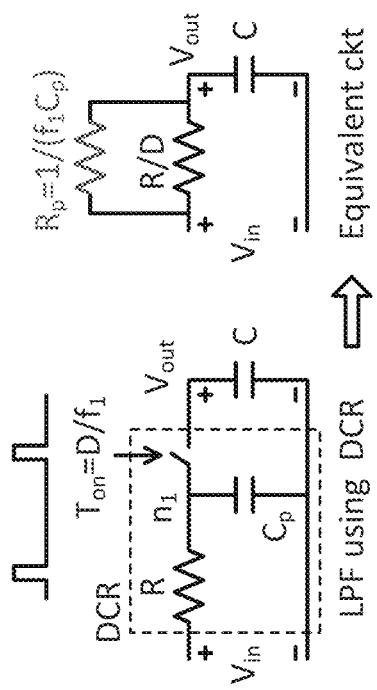
FIG. 1b illustrates an equivalent circuit of a low-pass filter using a duty-cycled resistor (DCR) in accordance with an embodiment of the invention.

Turning now to the drawings, high dynamic range, common-mode-interferer tolerant sensing front-ends for neuromodulation systems in accordance with various embodiments of the invention are illustrated. In many embodiments, the neuromodulation system uses a feed-forward common-mode cancellation (CMC) path to attenuate common-mode (CM) artifacts appearing at a voltage input, thus allowing for the simultaneous recording of neural data and stimulation of neurons. In many embodiments of the invention, the feed-forward CMC path is utilized to attenuate the common-mode swings at the input of the operational amplifier, $V_{in,CM}$, which can restore the linear operation of the front-end for differential signals.

Since the signals of interest may occupy frequencies as low as 1 Hz, a high-pass filter may be necessary with a corner frequency less than 1 Hz. Such low corner frequencies can be difficult to implement as they usually require very-large resistors and capacitors, making it prohibitively area expensive. Accordingly, many embodiments of the invention provide a Multi-rate Duty-Cycled Resistor (MDCR) to implement high-pass filters with low corner frequencies.

Accordingly, in several embodiments, the neuromodulation system utilizes an anti-alias filter (AAF) that includes a duty-cycles resistor (DCR) switching at a first frequency $f_1$, followed by a DCR switching at a second frequency $f_2$. The AAF allows for a significantly reduced second frequency $f_2$ that enables the multi-rate DCR to increase the maximum realizable resistance, which is dependent upon the frequency ratio $f_1/f_2$.

In several embodiments, the neuromodulation system introduces chopping in the auxiliary path in order to address a feedback problem in the auxiliary path. In particular, the auxiliary-path used in the prior art charges the input capacitor $C_{in}$ at the beginning of every chopping phase using aux-buffers, reducing the charge provided by the input to zero, thus boosting the input impedance $Z_{in}$ of the chopper amplifier.

In several embodiments, storage capacitors assist the aux-buffers at the beginning of the pre-charge phase by charge-sharing with $C_{in}$, and are disconnected for the remainder of the pre-charge phase. Hence, the input caps $C_{in}$ may be accurately charged to $V_{in}$ by the end of the pre-charge phase. Thus the settling error in the pre-charge phase may be reduced, leading to higher input impedance without increasing power consumption.

Systems and methods for implementing high dynamic range sensing front-ends for neuromodulation systems in accordance with various embodiments of the invention are discussed further below.

Bio-Signal Front-Ends

A neural signal recording system typically calls for a system that is small, fully implantable, consumes very low power while processing several channels, and can wirelessly transmit data to terminals such as (but not limited) to servers and/or a host computer. In addition, neuroscientists also seek the capability of recording neural data while simultaneously stimulating neurons. To preserve patient safety and compliance with FDA regulations, such systems face a unique set of design challenges.

Closed-loop neuromodulation with simultaneous stimulation and sensing is desired to administer therapy in patients suffering from drug-resistant neurological ailments. However, stimulation can generate large artifacts at recording sites, which can saturate traditional front-end systems used to record neural data. The common-mode (CM) artifact can be ~500 mV, and the differential-mode (DM) artifact can be 50-100 mV.

In many embodiments, a neuromodulation system is utilized that includes a neural recording chopper amplifier that can tolerate 80 $mV_{pp}$ DM and 650 $mV_{pp}$ CM artifacts in a signal band of 1 Hz-5 kHz. In several embodiments, a linearity of 80 dB is provided to enable digitization of a 2 $mV_{pp}$ neural signal to 8 bits accompanied by an 80 $mV_{pp}$ DM artifact. In many embodiments, the neural recording front-ends also function within a power budget of 3-5 µW/ch, an input-referred noise range of 4-8 $\mu V_{rms}$, and a DC input impedance range of $Z_{in}$>1 GΩ and have a high-pass cutoff of 1 Hz. Systems and methods for implementing high dynamic-range neural recording chopper amplifiers in accordance with various embodiments of the invention are discussed further below.

Figure 1C:
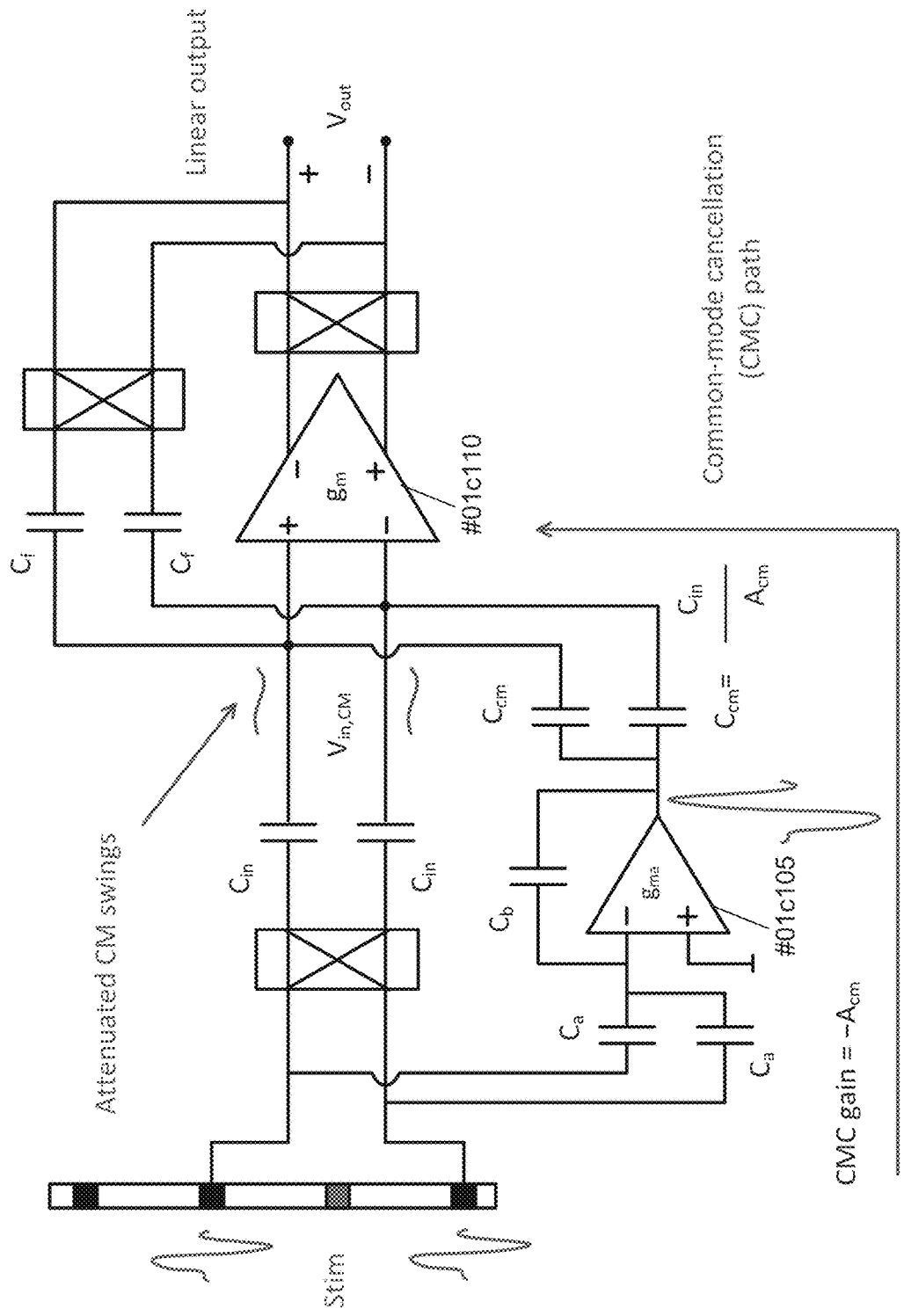
FIG. 1c illustrates a chopper amplifier with a common-mode cancellation (CMC) path in accordance with an embodiment of the invention.
Figure 1D:
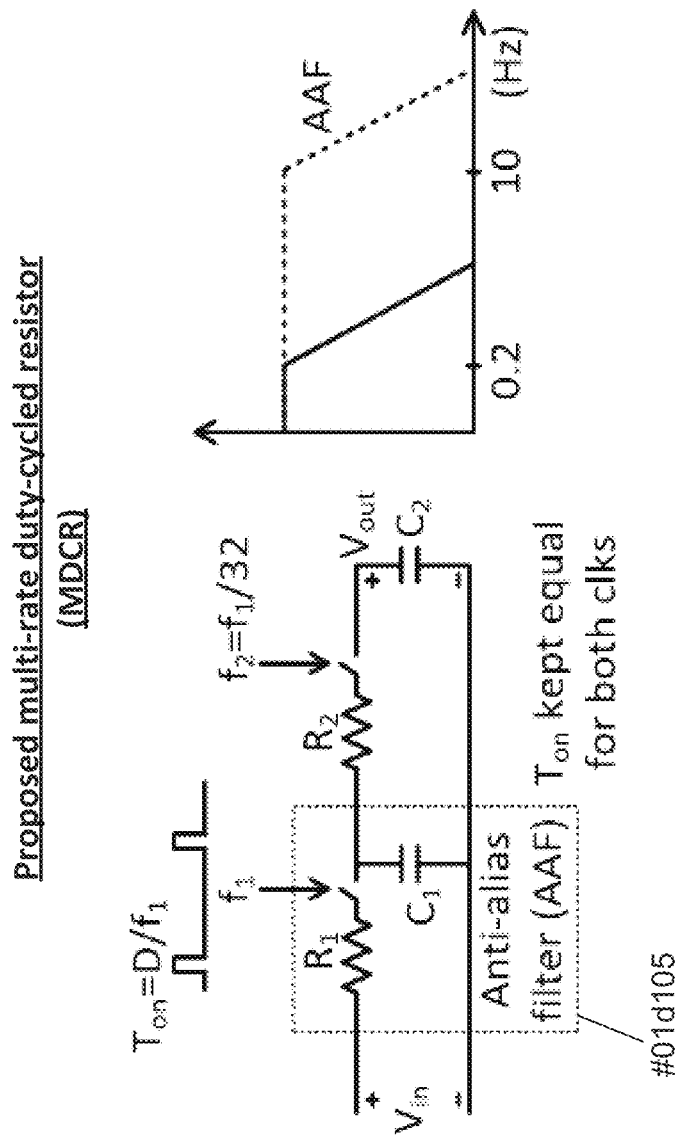
FIG. 1d illustrates a multi-rate duty-cycled resistor (MDCR) to realize large resistance while overcoming a limitation due to parasitic capacitance in accordance with an embodiment of the invention.
Figure 1E:
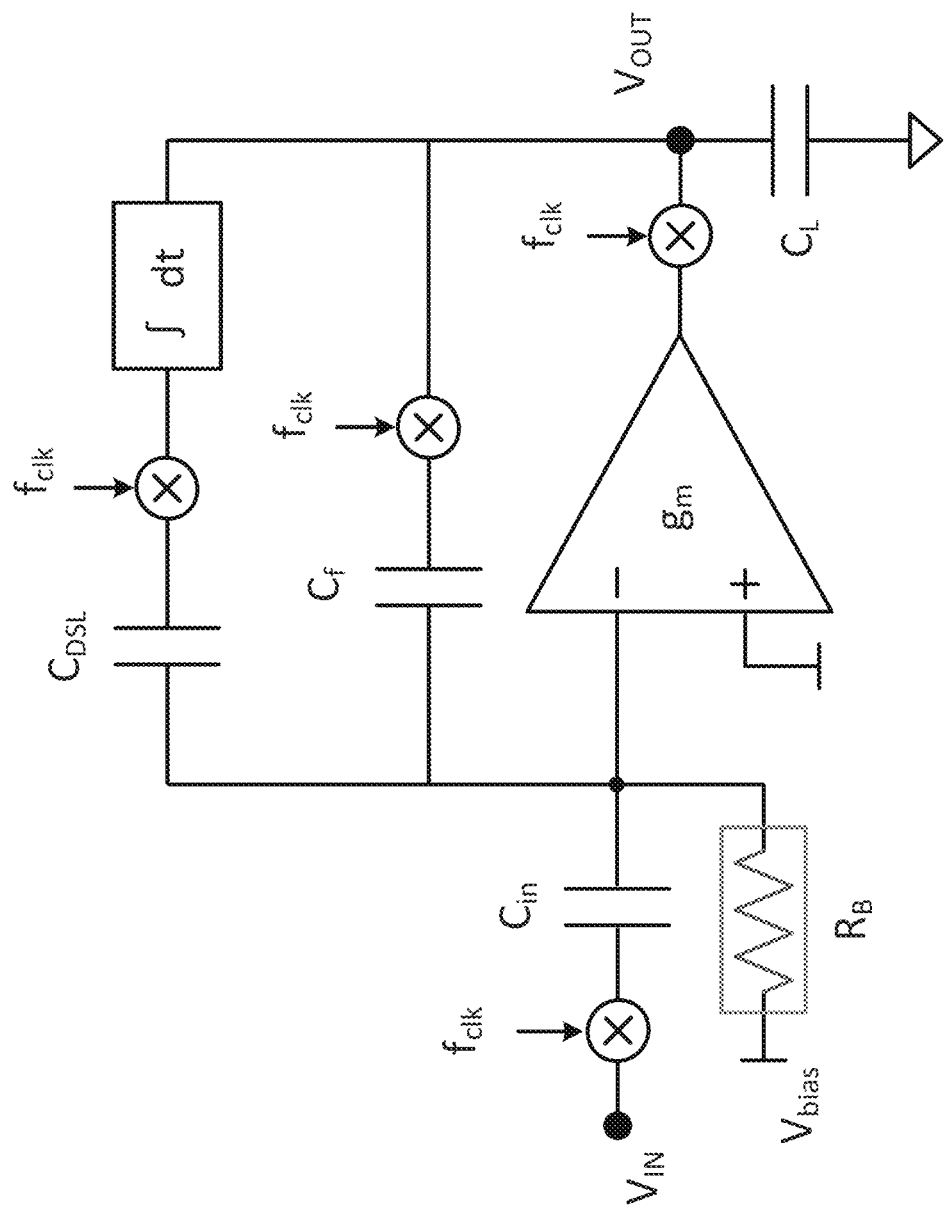
FIG. 1e illustrates a chopper amplifier with capacitive feedback and a servo-loop in accordance with an embodiment of the invention.
Figure 1F:
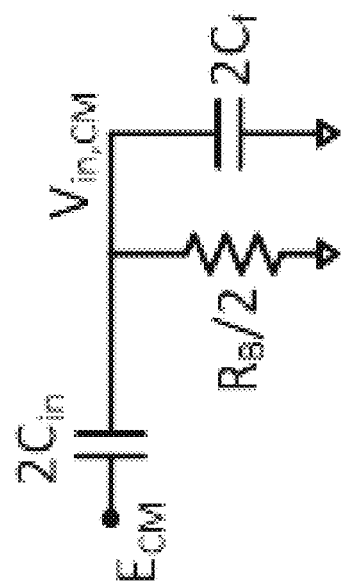
FIG. 1f illustrates an equivalent common-mode circuit for a chopper amplifier for common mode signals in accordance with an embodiment of the invention.

High Dynamic-Range Neural Recording Chopper Amplifier:

The susceptibility of conventional recording front-ends to common-mode interference can be appreciated by way of comparison of amplifiers implemented in accordance with various embodiments of the invention and typical chopper amplifiers, such as the conventional chopper amplifier illustrated in FIG. 1a. As illustrated in FIG. 1a the amplifier 1a100 can be implemented using capacitive feedback in the "inverting" topology. Chopping can be implemented using passive mixers 1a105 at the input and feedback arms of the capacitive feedback network. The demodulation mixer 1a110 is placed within the operational amplifier $g_m$ 1a115, usually in-between the 1$^{st}$ and 2$^{nd}$ stages of a 2-stage operational amplifier. The signals appearing at the electrode inputs consist of a differential signal with amplitudes <100 mV, and a common-mode signal with amplitudes up to 500 mV. Passive mixers may allow the common-mode signal to pass unaltered. The operational amplifier 1a115 used in the chopper amplifier 1a100 can be usually designed to respond only to differential signals while having high common-mode rejection. This can be accomplished by using a differential-pair with a high-impedance tail current source. Also, common-mode feedback (CMFB) loops can be used to set the bias voltages at the outputs of $g_m$. Hence, for common-mode signals, the CMFB loops create low-impedance connections to ac-ground at the output of $g_m$. To set the common-mode DC bias at the input of the operational amplifier 1a115, large resistors ($R_B$ in FIG. 1a) can be used. The equivalent common-mode circuit for a chopper amplifier in accordance with an embodiment of the invention is illustrated in FIG. 1f. The transfer function from the common-mode input at the electrode $E_{CM}$ to the operational amplifier input $V_{in,CM}$ is found to be $$\frac{V_{in,CM}}{E_{CM}} = \frac{\omega C_{in} R_B}{1 + \omega(C_{in} + C_f)R_B} \quad (1)$$

Figure 1G:
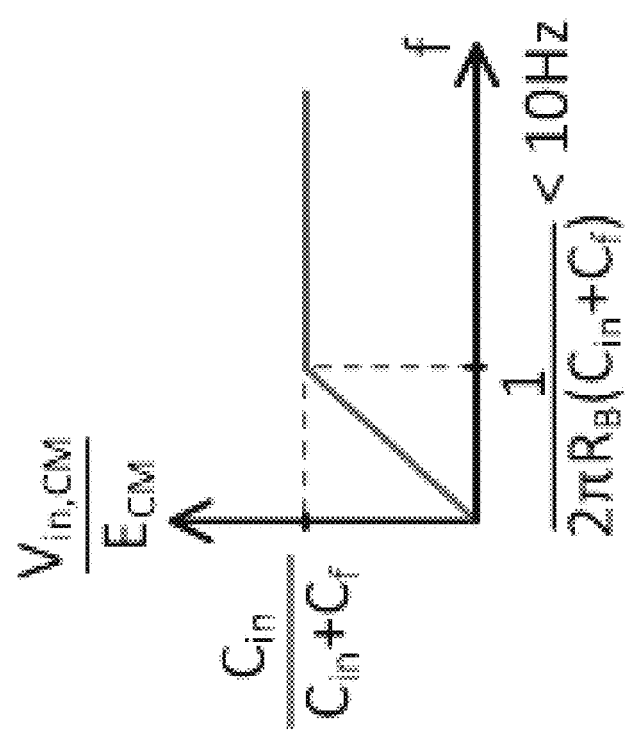
FIG. 1g plots a transfer function from the common mode input at an electrode to an operational amplifier input in accordance with an embodiment of the invention.
Figure 1H:
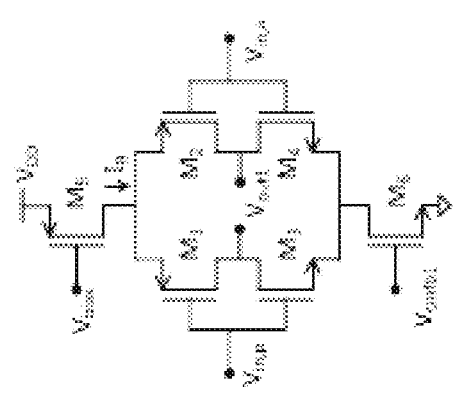
FIG. 1h illustrates a current-reuse operational amplifier in accordance with an embodiment of the invention.

The above transfer function is plotted in FIG. 1g. It is evident that $V_{in,CM}/E_{CM}$ is a $1^{st}$ order high-pass filter, with the corner frequency set by the capacitance $C_{in}+C_f$ and the resistor $R_B$. To ensure proper functioning of the chopper amplifier, this corner frequency can be usually set to <10 Hz. Hence, common-mode signals beyond 10 Hz pass unattenuated to the input of the operational amplifier, which could cause the differential response of a power-optimized amplifier to show significant departures from the expected response. Consider the current-reuse differential pair illustrated in FIG. 1h, which is the most common topology (due to its favorable power-noise trade-off) used for the $1^{st}$ stage of the operational amplifier $g_m$. To ensure sufficient headroom for the tail current sources, the gate bias $V_{in,CM}$ of the input transistors $M_{1-4}$ may need to be within the following range: $V_{ov6}+V_{GS3,4}<V_{in,CM}<V_{DD}-V_{ov5}-V_{GS1,2}$, where $V_{DD}$ is the supply voltage, $V_{ov5,6}$ are the overdrive voltages of the tail current sources and $V_{GS1-4}$ are the required gate-source voltages for transistors $M_{1-4}$ to carry a bias current of $I_B/2$. Assuming $V_{DD}$=1.2V, $V_{ov5,6}$=0.1V and $V_{GS1-4}$=0.45V (typical values), the range for $V_{in,CM}$ is 0.55V<$V_{in,CM}$<0.65V. Hence the input common-mode range may be limited to less than 100 mV. This range can be significantly lower than the common-mode swings (500 mV) that are expected at the electrodes. To estimate the distortion caused by common-mode artifacts, the chopper amplifier in FIG. 1e was simulated with a differential input of 80 mV$_{pp}$ at 1 kHz, along with a common-mode interferer of 500 mV$_{pp}$ amplitude at 900 Hz. The total harmonic distortion (THD) degraded from −74 dB to −43 dB when the common-mode interferer was enabled, thus exposing the severity of the problem.

A solution to the CM-interferer problem can be to use an operational amplifier with a large input common-mode range (ICMR), like a folded-cascode topology. Although the folded-cascode may consume more than twice the power as compared to the current-reuse operational amplifier (for the same noise), immunity to CM interference could be worth the power penalty. However, it must be noted that these CM interferers are not "slow" signals. Since the CM interferers have the same BW as the differential signals of interest, large CM swings at the input of operational amplifiers could lead to distortion. This can be particularly significant when the operational amplifier is designed for low-noise and low-power operation, i.e. the input devices (and possibly others) are biased in weak inversion, where they are most nonlinear. To verify this, a simulation was performed on a folded-cascode operational amplifier with an n-MOS input diff-pair, from a 1.2V supply with an ICMR of 0.7V. The following set up scenario was applied: differential input of 40 mV$_{pp}$ at 1 kHz, along with a common-mode interferer of 500 mV$_{pp}$ amplitude at 900 Hz. Since the CM interferer (0.5V) is smaller than the ICMR (0.7V), the linearity of the front-end could be preserved in the presence of the CM interferer. However, the total harmonic distortion (THD) degraded from −78 dB to −62 dB when the CM interferer was enabled. Thus it is evident that a simple folded-cascode with its large ICMR is insufficient.

Accordingly, the presence of large common-mode swings at the operational amplifier input $V_{in,CM}$ can lead to distorted outputs. In many embodiments of the invention, a feed-forward common-mode cancellation (CMC) path is utilized to attenuate the common-mode swings at $V_{in,CM}$, which can restore the linear operation of the front-end for differential signals. An example of a CMC path in accordance with an embodiment of the invention is illustrated in FIG. 1c. The common-mode signal at the electrodes can be sensed and amplified by the operational amplifier $g_{ma}$ 1c105 and capacitors $C_a$ and $C_b$. This amplified common-mode signal may then be subtracted from $V_{in,CM}$ through capacitors $C_{cm}$. The gain in the CMC path can be set by the capacitor ratio $A_{cm}$=2 $C_a/C_b$. If $C_{cm}$ is sized to be $C_{in}/A_{cm}$, then the common-mode signals at the input of the operational amplifier $V_{in,CM}$ can be ideally cancelled to zero. Any mismatches in the ratio of $C_{in}/C_{cm}$ may lead to residual common-mode swings at $V_{in,CM}$. However, since $g_m$ may be immune to small common-mode swings (<20 mV), a cancellation accuracy of 2% may be sufficient. This can be achieved by matching the capacitors $C_{in}$ and $C_{cm}$. However, the presence of the capacitors $C_{cm}$ may lead to an increase in the input-referred noise of the front-end, as shown by the following equation:

$$v_{n,in} = v_n \left[1 + \frac{C_{in} + C_{cm}}{C_f}\right] \quad (2)$$

Here, $v_n$ is the input-referred noise of the operational amplifier $g_m$ 1c110. To minimize the increase in the input-referred noise, $C_{cm}$ can be sized smaller than $C_{in}$ to provide a larger gain $A_{cm}$ in the CMC path. However, increasing $A_{cm}$ may result in larger signal swings at the output of $g_{ma}$ 1c105, which may cause saturation due to limited headroom at the output of $g_{ma}$. This may prevent the CMC path from cancelling the common-mode swings at $V_{in,CM}$. To increase the headroom at the output of $g_{ma}$ 1c105, many embodiments integrate a 50%-efficient charge-pump on-chip to generate a local 1.8V supply for $g_{ma}$ from the available 1.2V supply. Thus, with the CMC gain $A_{cm}$=2, common-mode signals as large as 650 mV$_{pp}$ can be easily cancelled at $V_{in,CM}$, while the noise contribution of $g_m$ is kept low. To achieve accurate cancellation, the bandwidth of the CMC path may need to be well beyond the expected bandwidth of the common-mode artifacts. Since it is expected that common-mode artifacts occupy the entire neural signal band up to 5 kHz, the CMC-path bandwidth is set to 30 kHz. This sets the requirement of $g_{ma}$ as follows:

$$g_{ma} \left(\frac{C_b}{C_b + 2C_a}\right) \frac{1}{2\pi(C_b + 2C_{cm})} > 30 \text{ kHz} \quad (3)$$

Figure 1I:
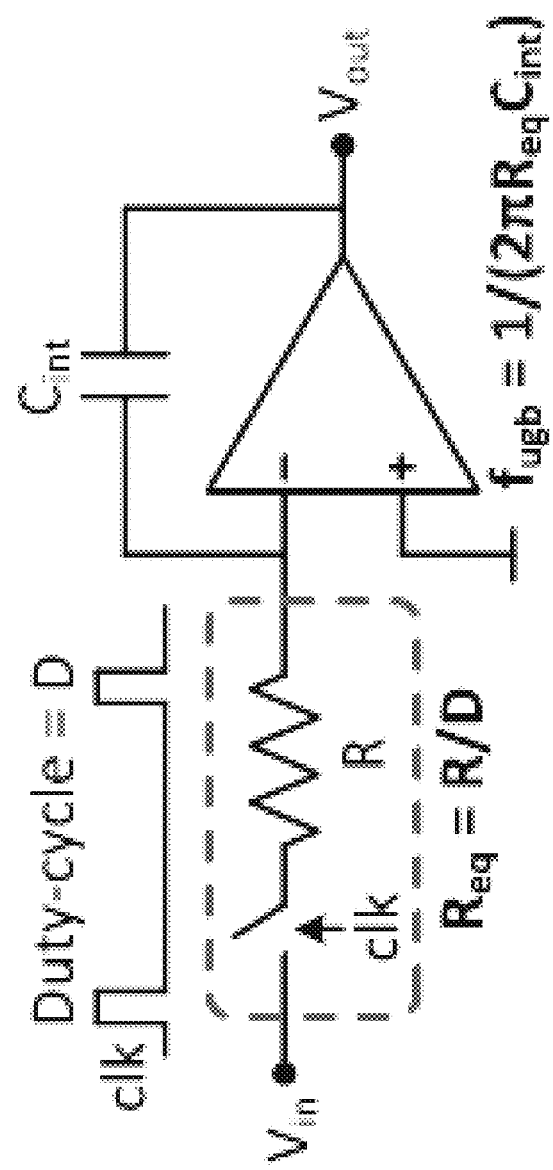
FIG. 1i illustrates a low-bandwidth integrator using a convention DCR in accordance with an embodiment of the invention.
Figure 1J:
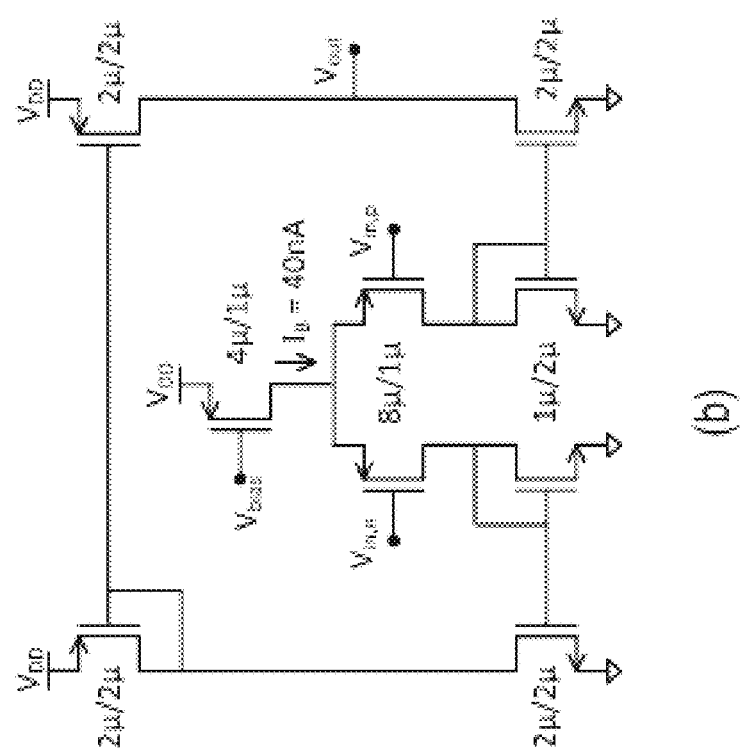
FIG. 1j illustrates a schematic of an operational amplifier used to realize $g_{ma}$ in accordance with an embodiment of the invention.

Hence, for $C_a$=$C_b$=1 pF and $C_{cm}$=0.5 pF, $g_{ma}$ should be larger than 1.13 µA/V. Although FIG. 1c illustrates a particular common-mode cancellation paths to attenuate common-mode swings at $V_{in,CM}$, any of a variety of CMC paths may be utilized as appropriate to the requirements of specific applications in accordance with embodiments of the invention. A schematic of an operational amplifier used to realize $g_{ma}$ in accordance with an embodiment of the invention is illustrated in FIG. 1j. A current of 120 nA can be sufficient to achieve the required $g_{ma}$, which is a small fraction of the overall power budget. Hence a relatively low efficiency (50%) charge-pump design was chosen for simplicity and reducing design time, since the power overhead is negligible.

Although the CMC path attenuates common-mode swings at $V_{in,cm}$, mismatches in $C_{cm}$ could degrade CMRR. However, since $C_{cm}$ is large (0.5 pF), good matching (<0.1%)

between $C_{cm}$ can be achieved by using common-centroid layout techniques. Any residual mismatches in $C_{cm}$ would indeed convert a common-mode signal at the electrode into a differential signal flowing out of the CMC path. However, note that there is no chopping at the output of the CMC path. Hence, the CM-to-DM signal at the CMC output remains at baseband, as compared to the up-modulated differential signal of the electrode. Thus, the CM-to-DM component remains separate (in frequency) from the desired differential signal, which ensures negligible impact to CMRR.

The neural signals at the electrodes (<1 mV) may be accompanied by electrode offsets as large as 50 mV. Hence any amplification may need to be applied only to the neural signals while attenuating the offset to prevent saturation. Since the signals of interest occupy frequencies as low as 1 Hz, a high-pass filter may be necessary with a corner frequency less than 1 Hz. Such low corner frequencies can be difficult to implement as they usually require very-large resistors and capacitors, making it prohibitively area expensive. Conventional capacitive-feedback amplifiers have been reported before that use "pseudo-resistors" as large resistors to realize sub-Hz high-pass corners. However, pseudo-resistors are unreliable due to its nonlinearity and sensitivity to process and temperature variations.

Figure 1K:
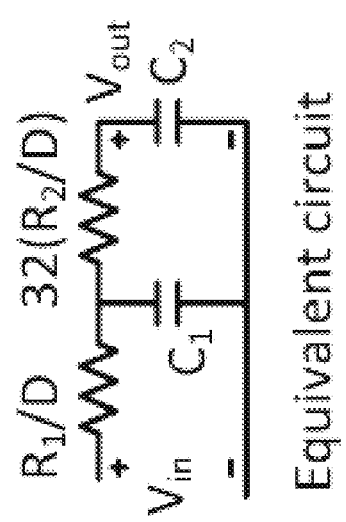
FIG. 1k illustrates an equivalent circuit of a composite low-pass filter in accordance with an embodiment of the invention.
Figure 1M:
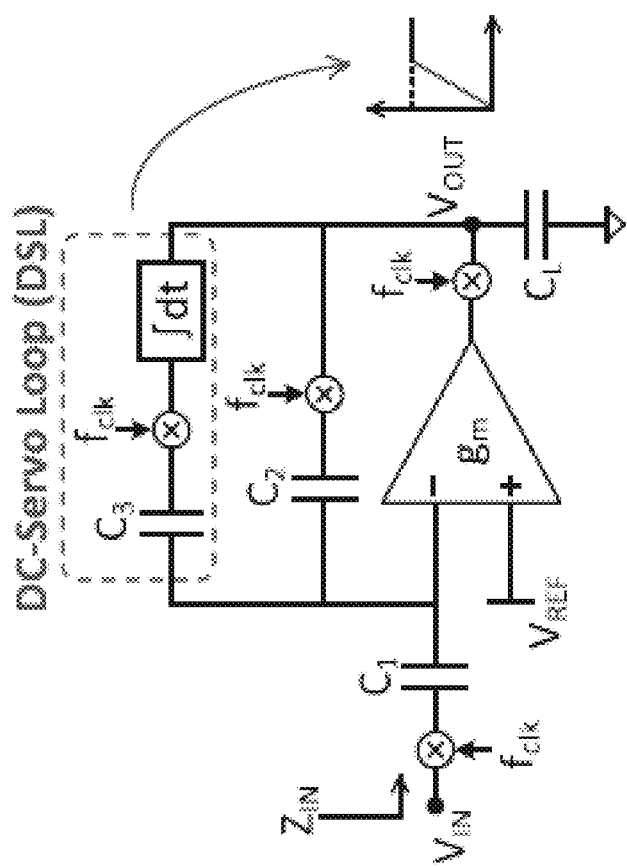
FIG. 1m illustrates a chopper amplifier with capacitive feedback and a servo-loop.

In chopper amplifiers, a DC-Servo loop can be used to realize the required high-pass corner frequency. The DC servo-loop consists of a low-bandwidth integrator that is placed in a negative feedback loop around the chopper amplifier, as illustrated in FIG. 1m. The high loop-gain of the servo-loop attenuates low-frequency signals at the output $V_{out}$, thus realizing the required high-pass corner. For frequencies beyond the unity-gain bandwidth of the servo-loop, the servo-loop is effectively broken. Hence, since the signal-band of interest lies beyond the servo-loop unity-gain bandwidth, the output noise of the servo-loop in the signal band will be amplified by $C_3/C_2$ and appear at $V_{out}$, as illustrated in FIG. 1m.

However, to achieve a sub-Hz high-pass corner frequency, a very-low bandwidth integrator may be necessary in the servo-loop. Prior implementations have used duty-cycled resistors (DCR) to realize such low-bandwidth integrators as illustrated in for example FIG. 1i. The DCR consists of a passive resistor R in series with a switch. When the switch is driven by a clock with a duty-cycle factor of D, the average resistance is amplified by 1/D. This amplified resistance can be used to realize the required low-bandwidth integrator for the servo-loop. The in-band noise contribution (when referred to the electrodes) of the DCR in the servo-loop can be reduced by realizing larger equivalent resistances R/D. Accordingly, the in-band noise of the DCR $R_B$ (FIG. 1e) can be reduced by realizing larger equivalent resistances. However, the maximum resistance of the DCR may be limited by the parasitic capacitance that appears in-between the passive resistor R and the switch as illustrated in FIG. 1b. This parasitic capacitance results in an equivalent switched-cap resistor $R_p$ that appears in parallel across the amplified resistance R/D, thus limiting the maximum equivalent resistance to $R_p$. The value of $R_p$ is given by $1/(f_1 C_p)$, where $C_p$ is the value of the parasitic capacitance and $f_1$ is the switching frequency of the DCR. As an example, for $C_p=5$ fF and $f_1=25$ kHz (both being typical values), $R_p$ is set to 8 GΩ. To increase $R_p$, either $f_1$ or $C_p$ can be reduced. However, $C_p$ may be limited by the substrate capacitance of the resistance R, while $f_1$ may need to be greater than twice the signal bandwidth to avoid aliasing. Thus it would seem that the maximum resistance is limited to 8 GΩ. Accordingly, many embodiments of the invention provide a Multi-rate Duty-Cycled Resistor (MDCR) to solve this problem. An example of an MDCR in accordance with an embodiment of the invention is illustrated in FIG. 1d. The following is based on an assumption of needing to realize a 0.2 Hz low-pass filter. Since such a low corner frequency may require an exceptionally large resistance (much larger than $R_p$ from FIG. 1b), many embodiments instead first realize a low-pass filter with a moderately low corner frequency of 10 Hz. This low-pass filter, termed the anti-alias filter (AAF) 1d105 in FIG. 1d, can be realized by the DCR formed by $R_1$ switching at $f_1$, and the capacitor $C_1$. The AAF 1d105 can be followed by a second low-pass filter formed by the DCR $R_2$ switching at $f_2$, and the capacitor $C_2$. The AAF may allow for a significantly reduced switching frequency $f_2$, as the AAF reduces the bandwidth of the signal flowing into the second low-pass filter. The lower limit on the switching frequency $f_2$ can be determined by the bandwidth $f_{aaf}$ of the AAF and the required attenuation of the aliased components. For this work, it was chosen to have $f_2/f_{aaf}$ to be greater than 64, which provides sufficient attenuation to the aliased components. Hence, in the second low-pass filter, the limitation of the minimum required switching frequency was circumvented by using the AAF, thus increasing the maximum realizable resistance of the DCR (formed by $R_2$ switching at $f_2$) by a factor of $f_1/f_2$. Although FIG. 1d illustrates a particular Multi-rate Duty-Cycled Resistor (MDCR) configuration, any of a variety of MDCR configurations may be utilized as appropriate to the requirements of specific applications in accordance with embodiments of the invention. An equivalent circuit of this composite low-pass filter in accordance with an embodiment of the invention is illustrated in FIG. 1k. The ON duration of the switches $T_{ON}$ is 5 ns, and $f_1$ was set to 23.44 kHz. This results in a duty-cycle factor D of 1/8530 for the DCR formed by $R_1$ switching at $f_1$. $R_1$ and $R_2$ were set to 350 kΩ, which leads to the equivalent resistance $R_{1,eq}=R_1/D=3$ GΩ. Thus, $R_{1,eq}$ along with $C_1=6$ pF leads to an anti-alias corner frequency $f_{aaf}$ of 10 Hz. In the second low-pass filter, $f_2$ is set to be $f_1/32=732.5$ Hz. This leads to the equivalent resistance $R_{2,eq}=(R_2/D)*32=90$ GΩ. Hence, $R_{2,eq}$ along with $C_2=12$ pF leads to the required low-pass corner frequency of 0.15 Hz. Thus by using the MDCR, a 350 kΩ resistance has been amplified to 90 GΩ.

Though the above example is a passive low-pass filter, an MDCR can also be used as a large resistor to realize low-bandwidth integrators. An example of an MDCR used as a large resistor in accordance with an embodiment of the invention is illustrated in FIG. 1l. The transfer function and noise analysis of the conventional DCR have already been discussed in H. Chandrakumar, D. Marković, "A High Dynamic-Range Neural Recording Chopper Amplifier for Simultaneous Neural Recording and Stimulation," in IEEE Journal of Solid-State Circuits, vol. 52, no. 3, pp. 645-656, March 2017, the entirety of which is herein incorporated by reference, and the results directly translate to the MDCR. Hence, the noise contribution of the MDCR is nearly identical to the noise contributed by the equivalent amplified resistance. By using the MDCR, a much larger resistance can be realized than what was possible using the conventional DCR, leading to lower noise in the front-end. Also, the MDCR can be realized in a small chip area, and there's no penalty on linearity unlike the pseudo-resistor.

Since an MDCR can be equivalent to a cascade of two low-pass filters such as the two-pass filter illustrated in FIG. 1k, it could cause instability when used in a feedback-loop since it introduces two poles. The servo-loop unity-gain bandwidth sets the high-pass corner $f_{HP}$ of the signal transfer function as illustrated in FIG. 1*m*. Let the servo-loop integrator have a unity-gain bandwidth of $f_{ugb,dsl}$. Hence, from FIG. 1*m*, $f_{HP} = f_{ugb,dsl}(C_3/C_2)$. To ensure stability, the AAF corner may need to be chosen to be much larger than $f_{HP}$, discussed further below.

Figure 10A:
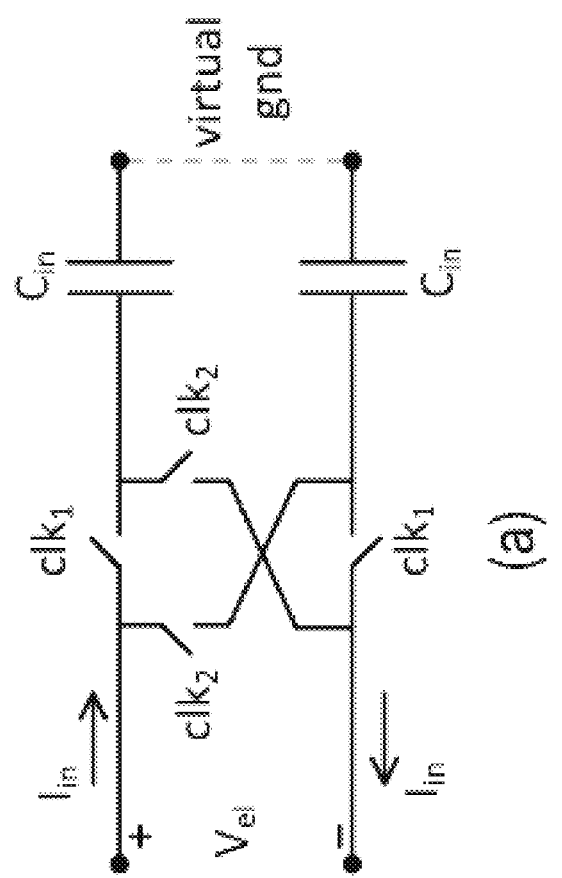
FIG. 10a illustrates an input arm of the chopper amplifier, consisting of capacitors $C_{in}$ and a passive mixer in accordance with an embodiment of the invention.
Figure 10B:
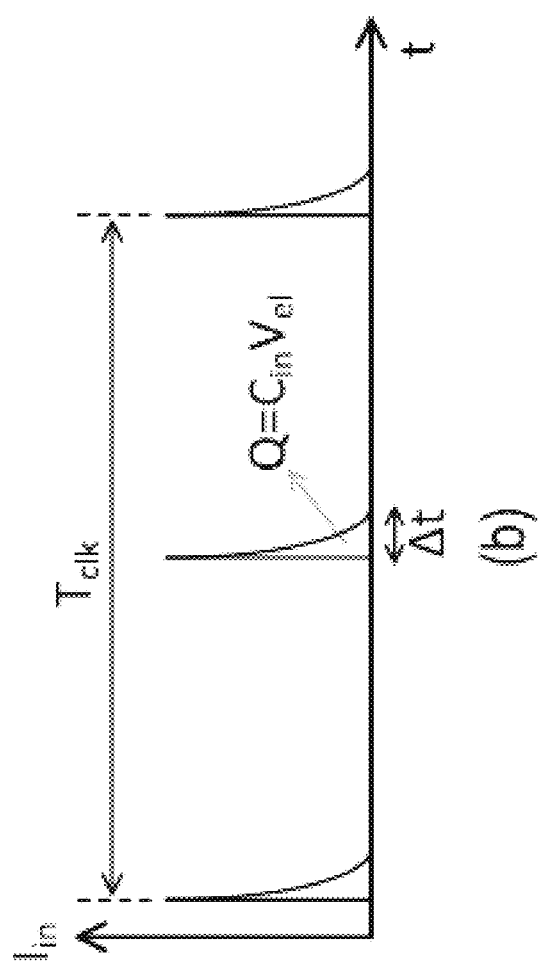
FIG. 10b illustrates a charge provided by an electrode during chopping in accordance with an embodiment of the invention.
Figure 10C:
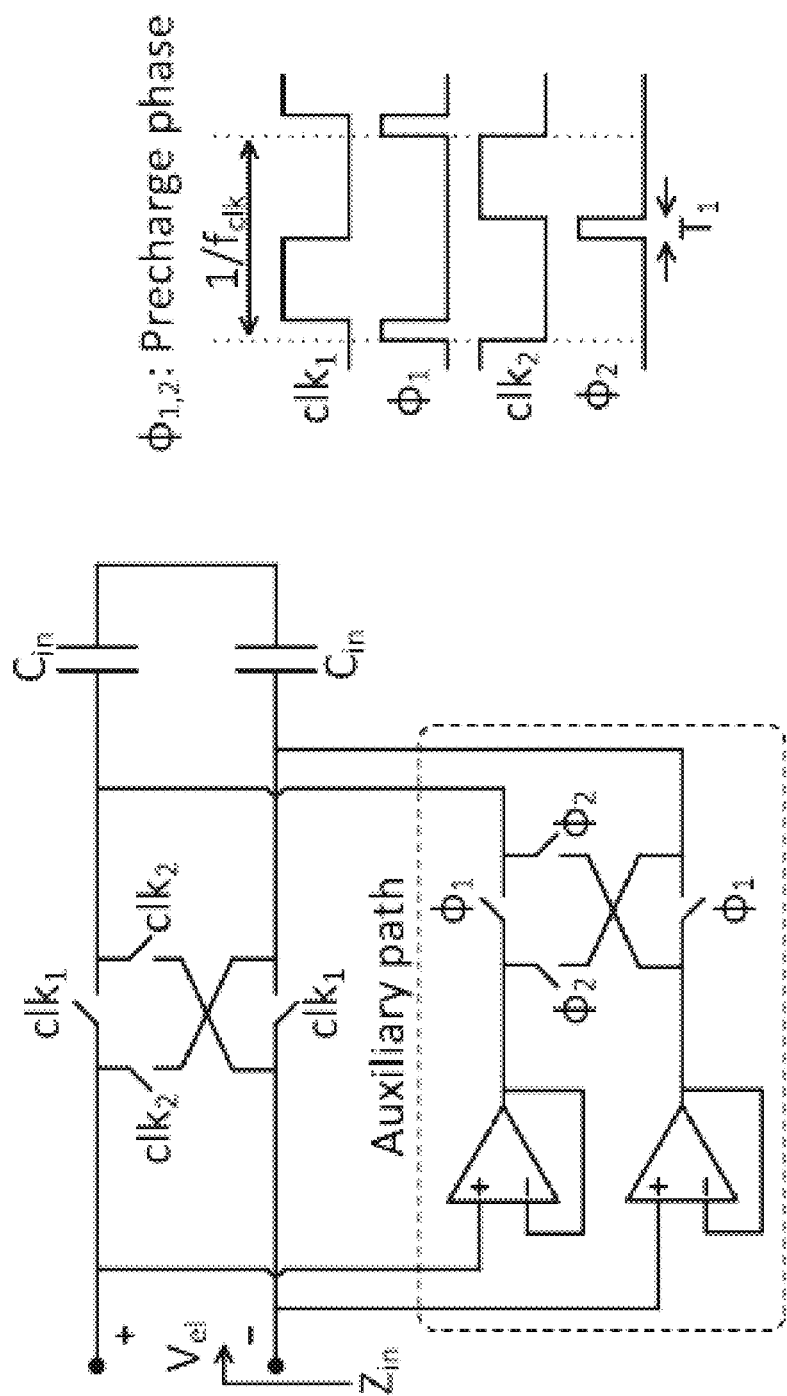
FIG. 10c illustrates an auxiliary path technique in accordance with an embodiment of the invention.
Figure 11:
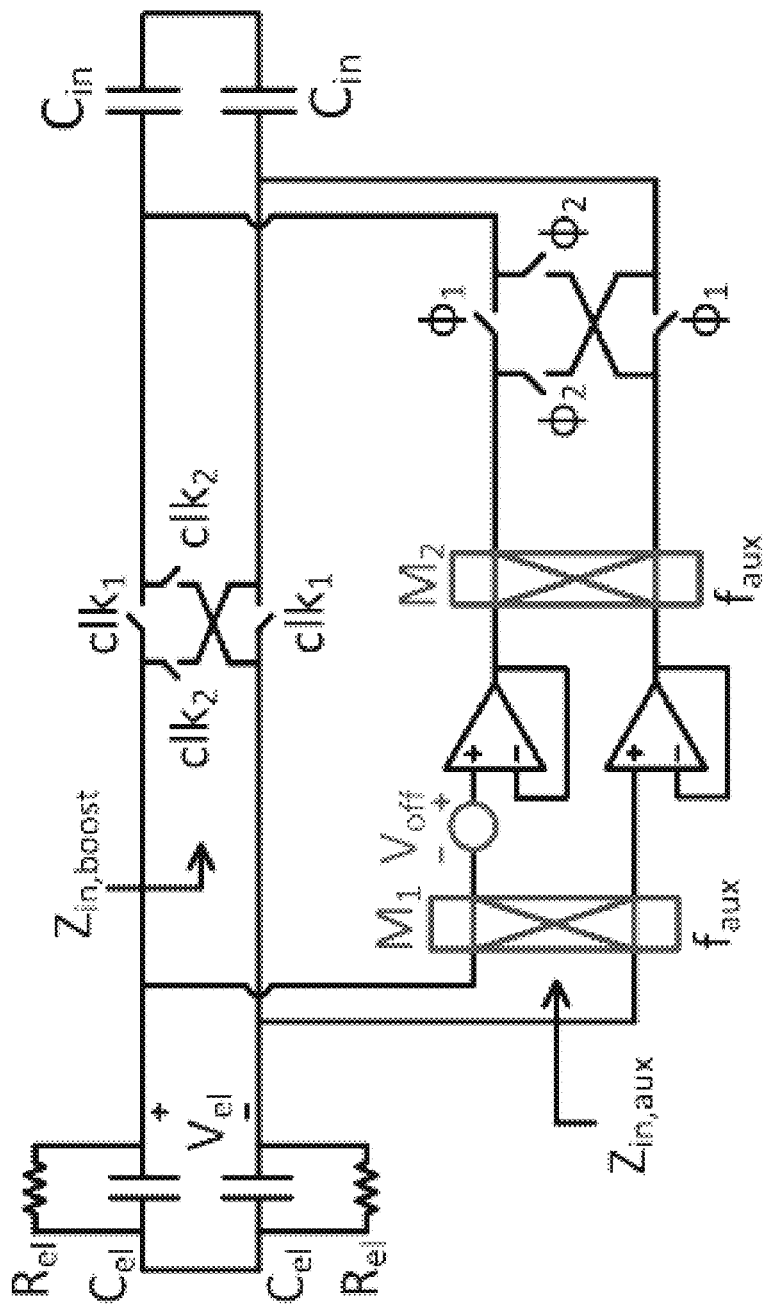

Auxiliary-Path for Boosting Input-Impedance:

The auxiliary-path to boost the input impedance $Z_{in}$ of a chopper amplifier is discussed in H. Chandrakumar, D. Marković, "A High Dynamic-Range Neural Recording Chopper Amplifier for Simultaneous Neural Recording and Stimulation," in IEEE Journal of Solid-State Circuits, vol. 52, no. 3, pp. 645-656, March 2017, the entirety of which is herein incorporated by reference. The input arm of the chopper amplifier, consisting of capacitors $C_{in}$ and the passive mixer in accordance with an embodiment of the invention is illustrated FIG. 10*a*. The charge provided by $V_{el}$ may be limited to a narrow time window (Δt in FIG. 10*b*) at the beginning of every chopping phase. If an alternate reservoir of charge (as opposed to the electrodes) could provide the charge required by $C_{in}$, then $Z_{in}$ can be increased. An auxiliary path technique in accordance with an embodiment of the invention is illustrated in FIG. 10*c*. An advantage of this technique is that the auxiliary path can be used simultaneously with the servo-loop, unlike the positive-feedback loop which is rendered inoperative by the servo-loop at low frequencies. The auxiliary path may also be immune to parasitic capacitance, which limits the maximum impedance that can be achieved by the positive feedback loop. However, this technique can have two limitations. First, it provided insufficient boost to $Z_{in}$, as described by H. Chandrakumar, D. Marković, "A High Dynamic-Range Neural Recording Chopper Amplifier for Simultaneous Neural Recording and Stimulation," in IEEE Journal of Solid-State Circuits, vol. 52, no. 3, pp. 645-656, March 2017 which reported a boosted $Z_{in}$ of 300 MΩ while many embodiment of the invention may need $Z_{in}$ larger than 1 GΩ. The second limitation is that this technique forms a positive feedback loop around the auxiliary path since the electrode is not an ideal voltage source. It can be shown that this positive feedback may cause the DC offset and flicker noise of the auxiliary-path buffers to be amplified and appear at the electrodes. Thus, the amplified offset could cause saturation, and the amplified flicker noise may degrade the performance of the front-end since it adds directly at the input of the front-end. The positive feedback in the auxiliary path is analyzed below. The differential half-circuit of the auxiliary path along with the input arm of the chopper amplifier in accordance with an embodiment of the invention is illustrated in FIG. 2*c*. The offset and flicker noise of the buffer can be modeled as a voltage source $V_{off}$, while the electrode impedance can be modeled by the impedance $R_{el}||C_{el}$. For simplicity, it is assumed that $R_{el}$ is infinite. In the pre-charge phase, the buffer charges the capacitor $C_{in}$ to $V_{el}+V_{off}$. At the end of the pre-charge phase, $C_{in}$ is re-connected back to $V_{el}$, and the electrode voltage is given by $$V_{el}(n+1) = V_{el}(n) + \left(\frac{C_{in}}{C_{in}+C_{el}}\right) \cdot V_{off}(n) \tag{4}$$

From the above equation, it is evident that the transfer function from $V_{off}$ to $V_{el}$ is identical to that of an ideal first-order integrator. Hence for a non-zero DC value of $V_{off}$, $V_{el}$ will go to infinity. To get a more accurate description of the positive feedback, the effect of a finite $R_{el}$ is considered next. From FIG. 2*c*, the capacitance $C_{in}$ can be periodically switched between the buffer output and the electrode. Hence, this switching capacitance forms an equivalent resistance, as illustrated in FIG. 2*d*, with a value of $R_a = T_c/(2 C_{in})$, where $T_c$ is the chopping period. Thus the buffer output $V_a = V_{el} + V_{off}$, and $V_{el} = V_a \cdot Z_{el}/(Z_{el}+R_a)$. Using these 2 equations, the transfer function $V_{el}/V_{off}$ is determined to be $$\frac{V_{el}}{V_{off}}(s) = \frac{2R_{el}C_{in}}{T_c(1+sR_{el}C_{el})} \tag{5}$$

Figure 2A:
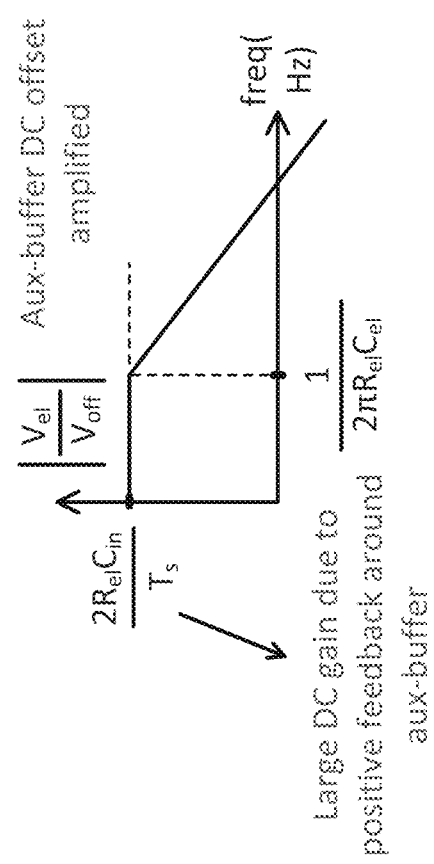
FIG. 2a illustrates a transfer function in accordance with an embodiment of the invention.

The above transfer function is shown in FIG. 2*a*. The DC gain is given by $2 R_{el}C_{in}/T_c$. Assuming $R_{el}=200$ MΩ, $C_{in}=1$ pF, $C_{el}=1$ nF and $T_c=40$ μs (all typical values), the DC gain from $V_{off}$ to $V_{el}$ is 10. Hence, a 5 mV auxiliary-buffer offset is amplified to a 50 mV DC voltage by the positive feedback in the auxiliary path, and this voltage appears at the electrodes. Also, from the transfer function in FIG. 2*a*, it reveals that low-frequency components of $V_{off}$, for example the flicker noise of the auxiliary-buffers, may also be amplified and appear at the electrodes, thus degrading the low-frequency noise performance of the front-end.

Figure 11:
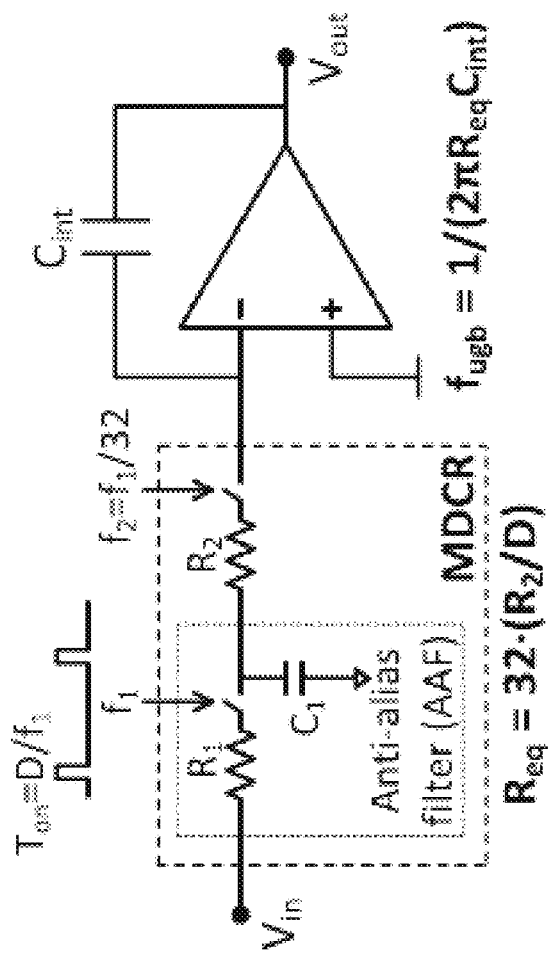
FIG. 11 illustrates an auxiliary-path chopping using mixers $M_{1,2}$ to mitigate the effect of positive feedback in accordance with an embodiment of the invention.

A solution to this problem can be determined by taking a closer look at the transfer function in FIG. 2*a*. The unity-gain bandwidth (UGB) of this transfer function is given by $\alpha f_c/\pi$, where a is the ratio given by $C_{in}/C_{el}$. For the above-chosen typical values of $C_{in}$ and $C_{el}$, the UGB of $V_{el}/V_{off}$ is approximately given by $f_c/3000$. Thus, if $V_{off}$ can be up-modulated to a frequency that is much larger than $f_c/3000$, then $V_{off}$ will appear as tiny ripples at the electrode instead of a large DC voltage. This is realized by introducing passive mixers $M_{1,2}$ in the auxiliary path as illustrated in FIG. 11. The frequency of the ripple at the electrodes will be equal to the clock frequency $f_{aux}$ used in the mixers $M_{1,2}$. To ensure that these ripples remain outside the frequency band of interest, $f_{aux}$ should be larger than 5 kHz. The amplitude of the ripples can be determined to be $$V_{ripple} \approx V_{off}\left(\frac{4}{\pi^2}\right)\frac{\alpha f_c}{f_{aux}} \tag{6}$$

Although introducing mixers $M_{1,2}$ can mitigate the amplification of $V_{off}$, it will reduce the input impedance of the front-end. This is because the gate capacitance of the auxiliary-path buffers along with the mixer $M_1$ will appear as a switched-cap resistance $Z_{in,aux}$ at the input of the front-end. Hence the input impedance of the front-end is now given by $Z_{in,boost}||Z_{in,aux}$, where $Z_{in,boost}$ is the boosted input impedance achieved by the auxiliary path, as illustrated in FIG. 11. To achieve the required 1 GΩ DC input impedance, $Z_{in,aux}$ may need to be significantly larger than 1 GΩ. $Z_{in,aux}$ is given by $1/(2 C_{auxbuf}f_{aux})$, where $C_{auxbuf}$ is the gate capacitance of each auxiliary-path buffer. Since $f_{aux}$ has a minimum value of 5 kHz, $C_{auxbuf}$ may need to be reduced to achieve the required value of $Z_{in,aux}$. However, reducing $C_{auxbuf}$ can be achieved by reducing the area of the input transistors of the auxiliary buffers, which may lead to a larger value of $V_{off}$ due to increased mismatch. This may cause larger ripples at the electrode (from equation 6) which is undesirable. Hence while sizing the input transistors of the auxiliary-buffers, the trade-offs for the input impedance and the ripple amplitudes at the electrode may need to be considered together. $V_{off}$ is proportional to $1/\sqrt{C_{auxbuf}}$ and the ripple amplitude can be proportional to $V_{off}/f_{aux}$. Thus, accounting for all trade-offs, the ripple amplitude $V_{ripple}$ can be proportional to $Z_{in,aux} \cdot \sqrt{C_{auxbuf}}$. Hence for a given $Z_{in,aux}$, $C_{auxbuf}$ may need to be minimized to reduce ripple amplitudes at the electrodes. This corresponds to using minimum-sized devices for the input transistors of the auxiliary-buffers. $C_{auxbuf}$ may ultimately be limited by routing capacitance. Hence a practical solution may be to reduce the gate capacitance of the input devices of the auxiliary buffers to match the routing capacitance between the gate and the mixer $M_1$. The mixers $M_{1,2}$ can be driven with a clock frequency of $f_c/4$, where $f_c=23.44$ kHz is the chopping frequency of the chopper amplifier. The input transistors of the auxiliary buffers can be sized such that $C_{auxbuf}$ (including routing capacitance) is about 15 fF, which sets $Z_{in,aux}$ to be about 6 GΩ. Hence $Z_{in,aux}$ is sufficiently large to achieve the required input impedance of the front-end.

Figure 2B:
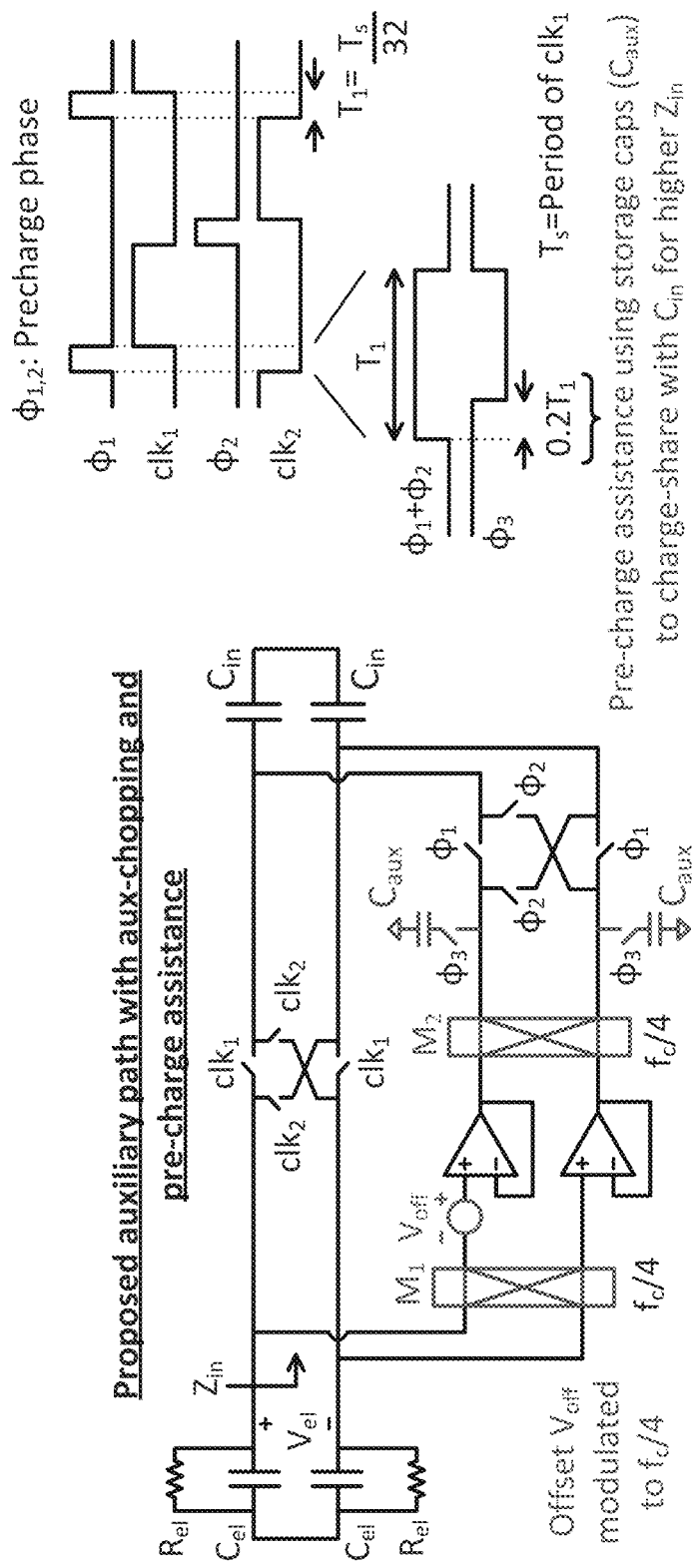
FIG. 2b illustrates implementation of auxiliary-buffer assistance using storage caps in accordance with an embodiment of the invention.
Figure 2C:
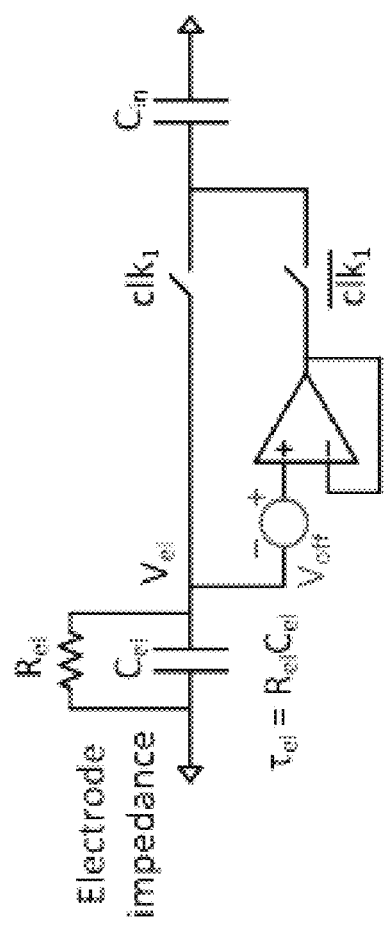
FIG. 2c illustrates a half-circuit of an auxiliary path to analyze positive feedback in accordance with an embodiment of the invention.
Figure 2D:
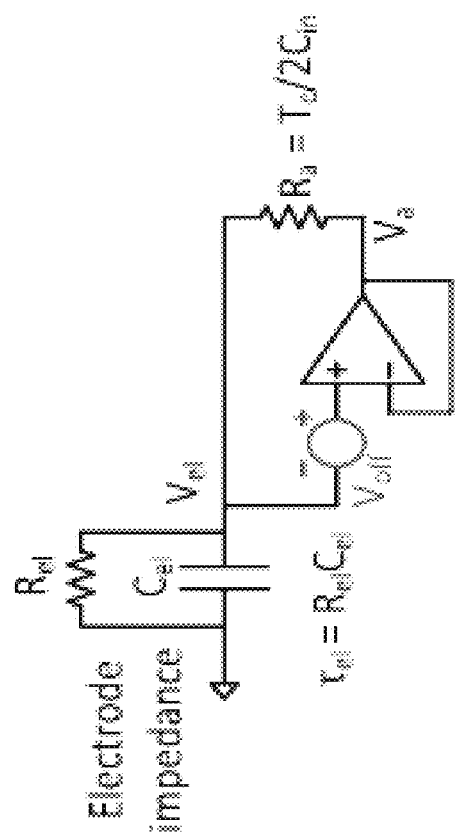
FIG. 2d illustrates an equivalent circuit using switched-cap approximation in accordance with an embodiment of the invention.
Figure 2E:
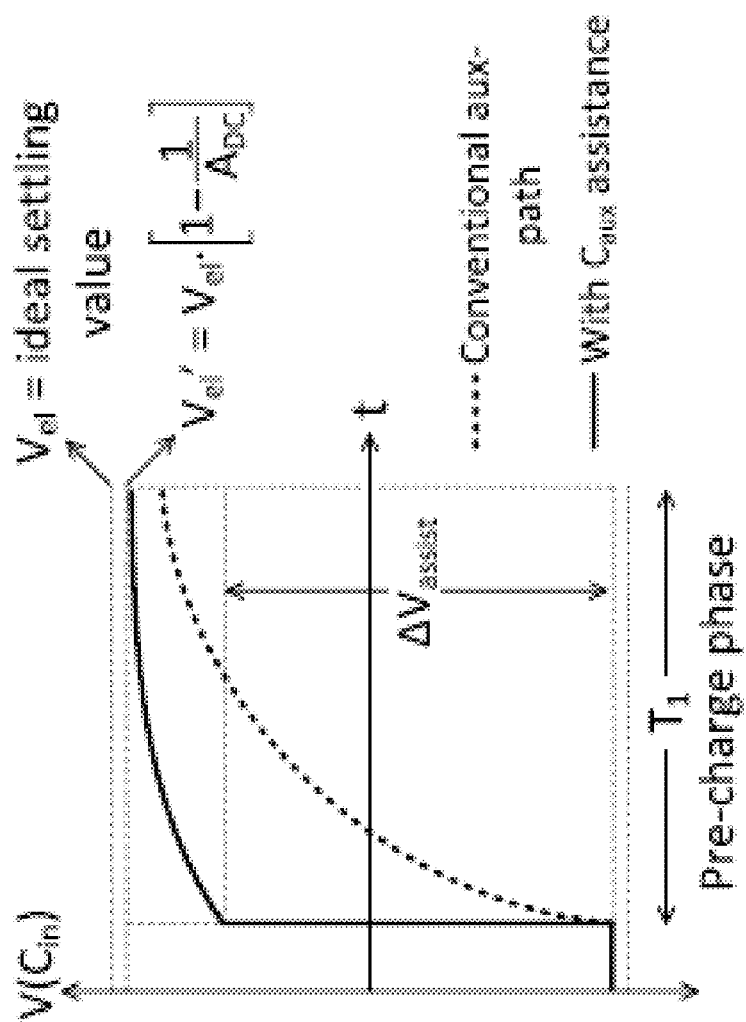
FIG. 2e illustrates setting errors in a precharge phase leading in accordance with an embodiment of the invention.

As discussed before, a limitation of the auxiliary path was the limited boost to $Z_{in}$. This limitation was due to the limited bandwidth of the auxiliary-buffers, which caused a non-zero settling error in the pre-charge phase. The finite gain of an operational amplifier used in the auxiliary-buffers may also lead to a non-zero settling error in the pre-charge phase. This is illustrated in FIG. 2e (with reference to FIG. 10c). The input-impedance at DC was derived in H. Chandrakumar, D. Marković, "A High Dynamic-Range Neural Recording Chopper Amplifier for Simultaneous Neural Recording and Stimulation," in IEEE Journal of Solid-State Circuits, vol. 52, no. 3, pp. 645-656, March 2017, and is restated here for completeness:

$$Z_{in,DC} = \frac{1}{2C_{in}f_{clk}} \left( \frac{1}{1/A_{DC} + \exp(-T_1/\tau)} \right) = Z_O \cdot \frac{A_{DC} \exp(T_1/\tau)}{A_{DC} + \exp(T_1/\tau)} \quad (7)$$

In the above equation, $\tau^{-1}$ rad/sec is the bandwidth of the auxiliary buffer, and $A_{DC}$ is the open-loop DC gain of the buffer, which is usually around 40 dB. This implies that the maximum achievable boost to $Z_{in}$ may be limited to a factor of 100. To ensure getting the most of this impedance boost, the settling error due to the finite bandwidth of the auxiliary-buffer may need to be minimized. This can be done by increasing the transconductance of the auxiliary-buffers, which would increase power consumption. An alternative is to use storage capacitors $C_{aux}$, as illustrated in FIG. 2b, to assist the auxiliary-buffers. At the beginning of the pre-charge phase (as shown in the timing diagram in FIG. 2b), $C_{aux}$ is allowed to charge-share with $C_{in}$. If $C_{aux}$ is sized to be significantly larger than $C_{in}$, then most of the pre-charging of $C_{in}$ (labeled as $\Delta V_{assist}$ in FIG. 2e) is complete in this charge-sharing phase. Hence the auxiliary-buffers now may only need to complete the remainder of the pre-charging of $C_{in}$. This may reduce the settling error in the pre-charge phase, leading to a larger $Z_{in}$ without increasing power consumption. $C_{aux}$ may be set to 8·Cin, and the DC current in the auxiliary-buffers may be 150 nA. This may be sufficient to provide an impedance boost by 2.5×, as described in detail below. From FIG. 2b, when $\varphi_{1,2}=0$, the auxiliary-buffer bias currents may be reduced to 25 nA to save power while ensuring that $C_{aux}$ tracks $V_{el}$ till the next pre-charge phase.

Figure 3A:
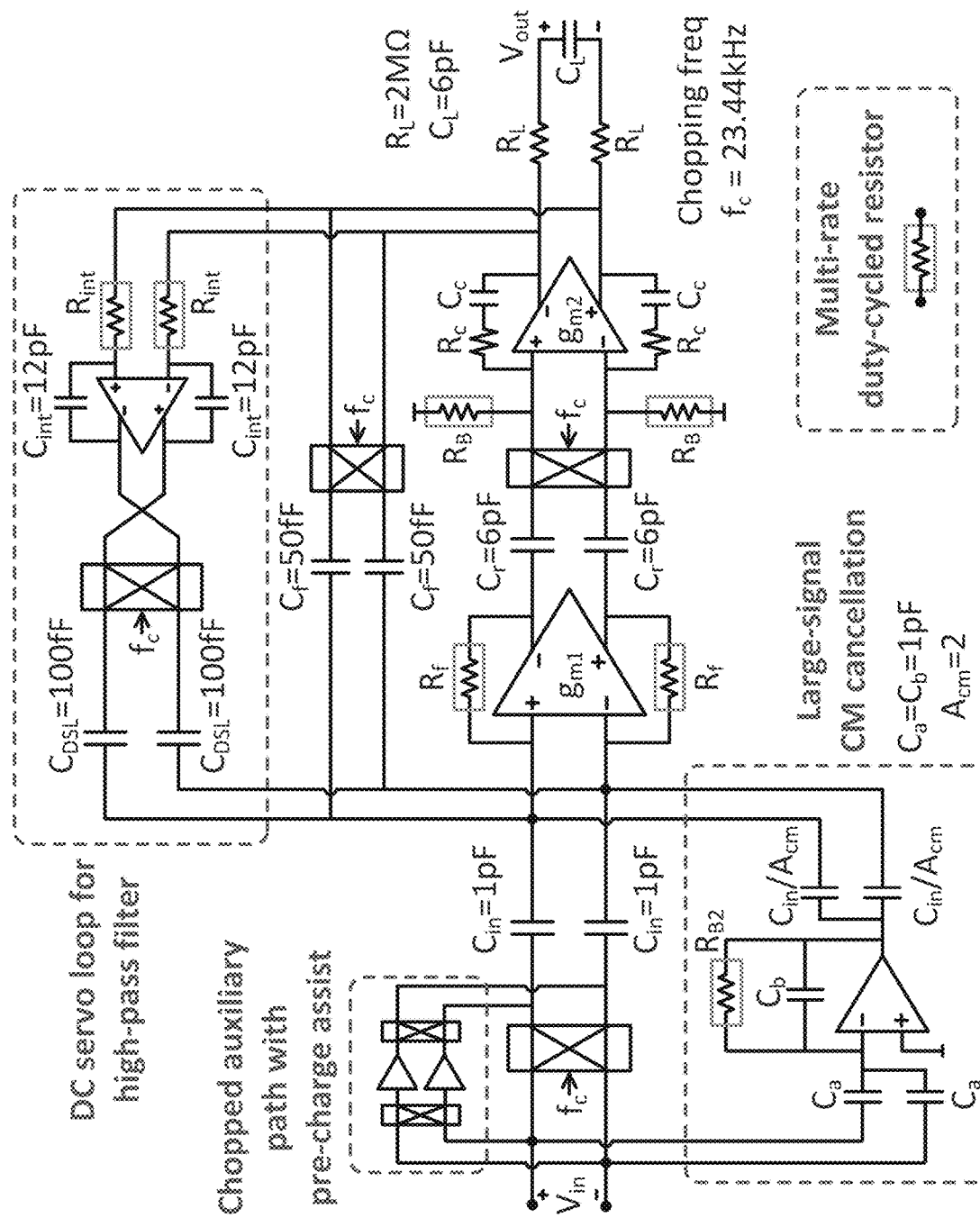
FIG. 3a illustrates a complete implementation of a front-end chopper amplifier in accordance with an embodiment of the invention.
Figure 3B:
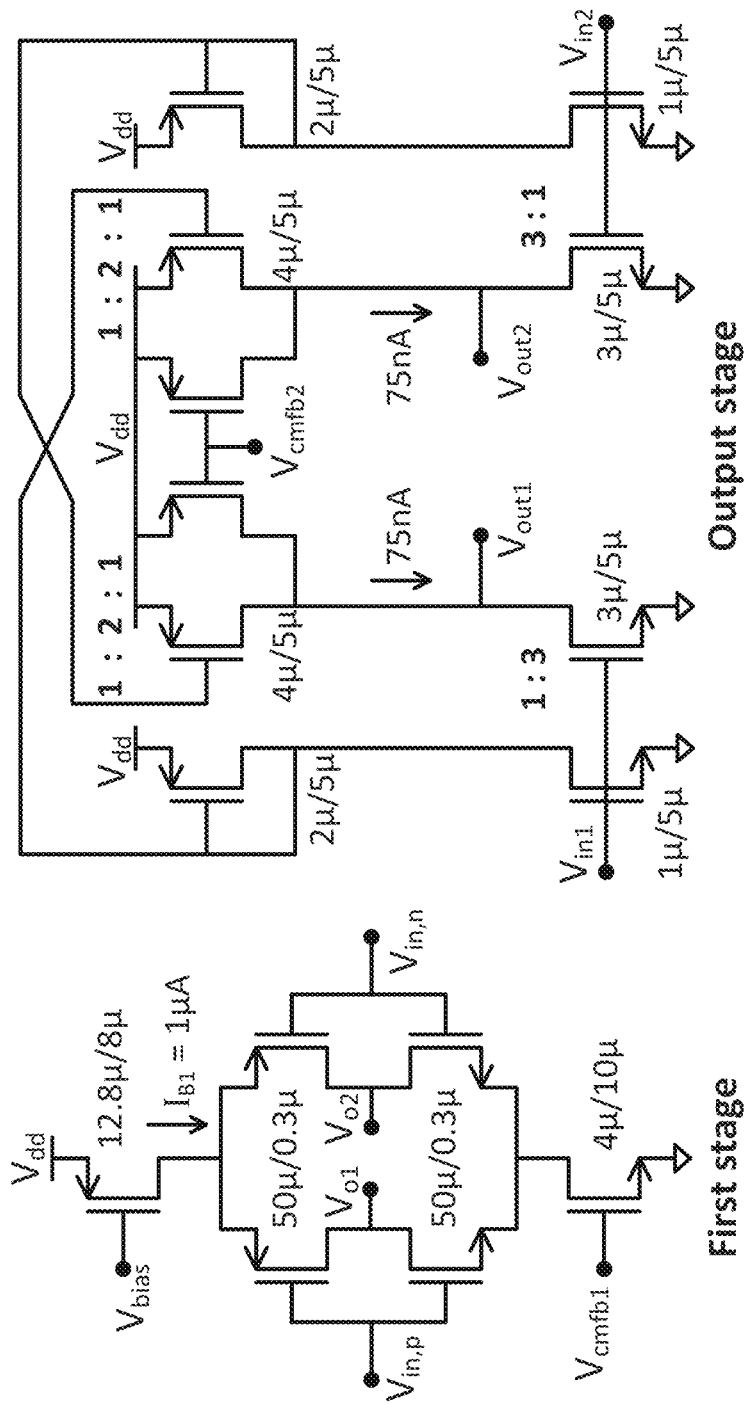
FIG. 3b illustrates schematics for operational amplifier $g_{m1}$ and operational amplifier $g_{m2}$ in accordance with an embodiment of the invention.

A chopper amplifier in accordance with an embodiment of the invention is illustrated in FIG. 3a, and the schematics for $g_{m1}$ and $g_{m2}$ are shown in FIG. 3b. In particular, FIG. 3a illustrates a chopper amplifier for spike and local field potential (LFP) recording in accordance with an embodiment of the invention. In many embodiments, the chopping frequency $f_c$ is 23.44 kHz. The mid-band gain may be set by $C_{in}/C_f=20$, and DC-blocking caps $C_r$ may be used to avoid chopper ripple at $V_{out}$. In several embodiments, the servo-loop uses multi-rate duty-cycled resistors with a 10 Hz anti-alias filter, $T_{on}=5$ ns, $f_1=23.44$ kHz and $f_2=732.5$ Hz, which boosts a 350 kΩ poly-resistor to $R_{int}=90$ GΩ. Since $C_{int}=12$ pF, the servo-loop integrator BW is 0.15 Hz. In many embodiments, the chopper amplifier is fabricated in a 40 nm CMOS technology. Although any of a variety of semiconductor processes can be utilized to implement a chopper amplifier as appropriate to the requirements of a given application in accordance with various embodiments of the invention. Although FIG. 3a illustrates a particular chopper amplifier configuration, any of a variety of processes and configurations may be utilized for chopper amplifiers as appropriate to the requirements of specific applications in accordance with certain embodiments of the invention.

Figure 7A:
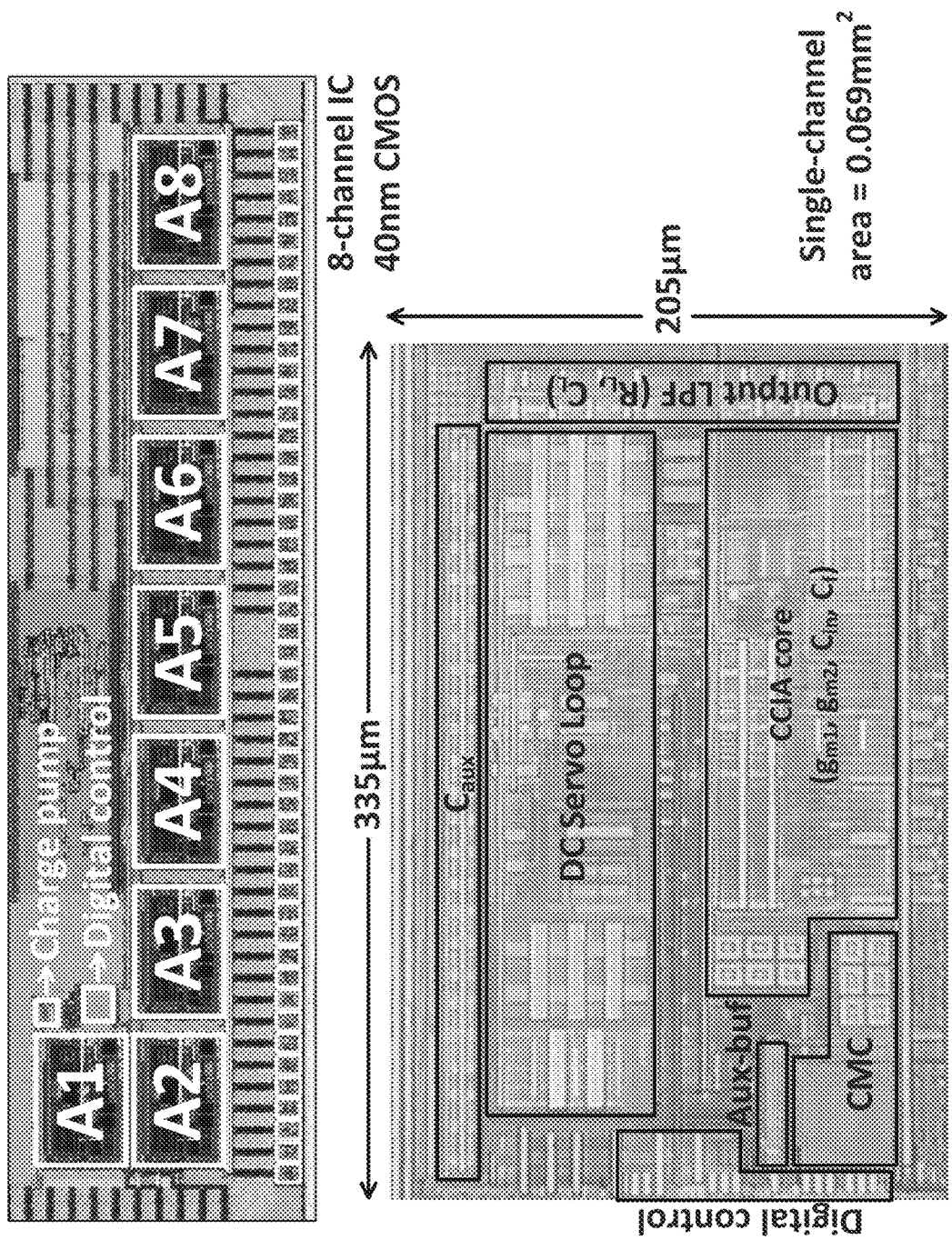
FIG. 7a illustrates a micrograph of a fabricated prototype showing eight chopper amplifiers implemented in 40-nm CMOS in accordance with an embodiment of the invention.
Figure 7B:
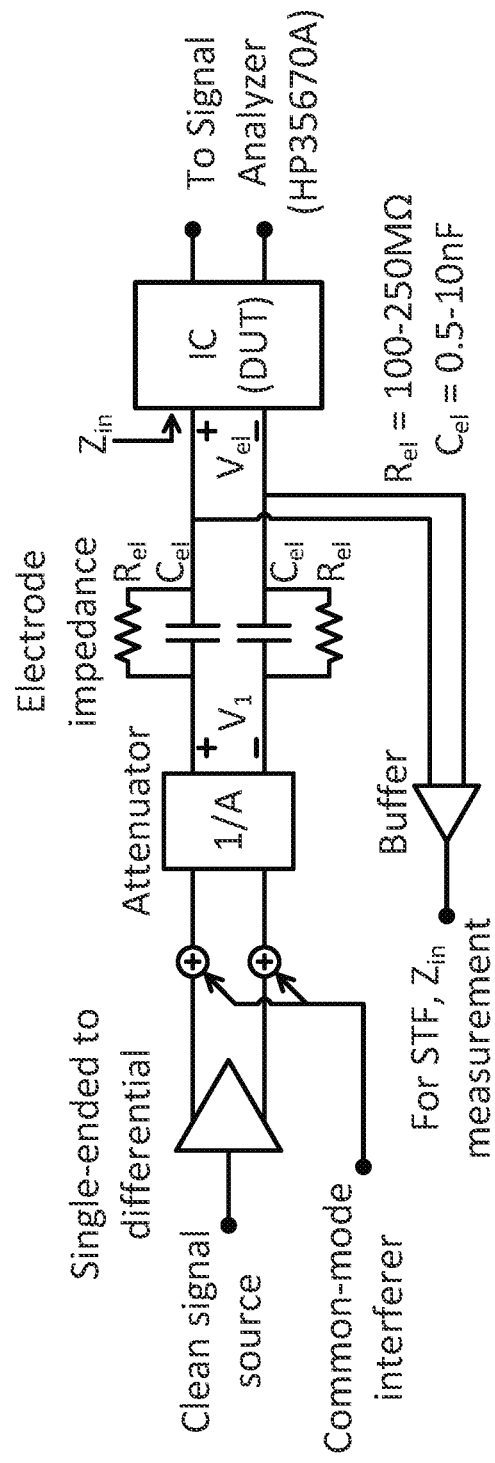
FIG. 7b illustrates a test setup for characterizing a fabricated chopper amplifier in accordance with an embodiment of the invention.

In several embodiments, an amplifier can be implemented in a 40-nm CMOS technology. FIG. 7a and FIG. 7b show a chip micrograph and the measurement setup with provisions to emulate the electrode impedance in accordance with an embodiment of the invention. The amplifier occupies an area of 0.069 mm²/ch and the total power consumed from a 1.2V supply is 2.8 µW. The transconductances $g_{m1}$ and $g_{m2}$ consume 1.2 and 0.25 µW respectively. The servo-loop, aux-path buffers and the CMC path consume 0.36, 0.2 and 0.3 µW respectively. Biasing and control-signal generation consumes 0.45 µW.

Figure 4A:
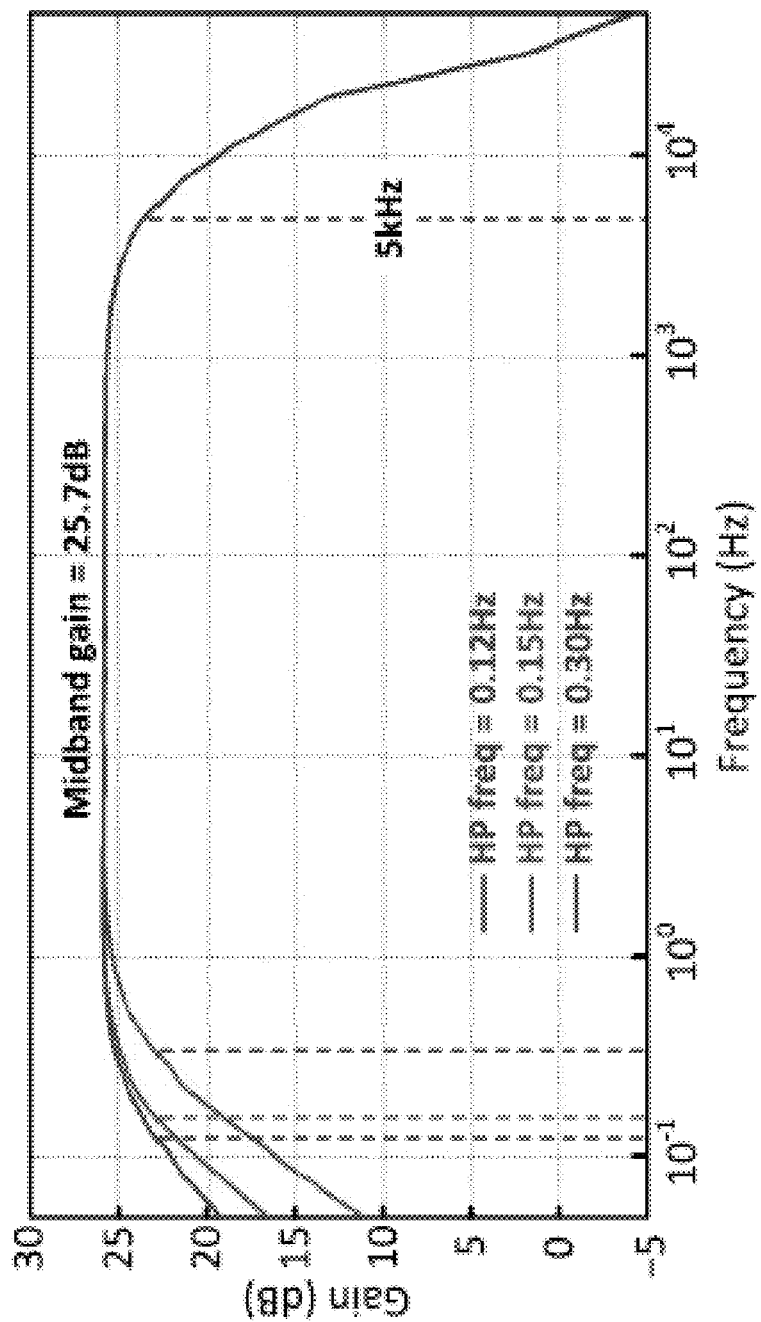
FIG. 4a illustrates a measured signal transfer function of a fabricated chopper amplifier, with programmable high-pass corner frequency in accordance with an embodiment of the invention.

The measured signal transfer function is shown in FIG. 4a. The mid-band gain can be 25.7 dB and the low-pass corner can be 5 kHz. The servo-loop unity-gain bandwidth sets the high-pass corner of the signal transfer function. From FIG. 3a, it is evident that $f_{HP}=2 f_{ugb,dsl}$. The high-pass corner $f_{HP}$ can be programmable from 0.12 Hz to 0.3 Hz by varying the duty-cycle factor in the MDCR. The AAF corner frequency in the MDCR can be chosen to be 10 Hz (Section IV-B). Hence, the pole associated with the AAF may be a non-dominant pole since it is far away from the unity-gain frequency $f_{HP}$ of the servo-loop, and the phase margin of the servo-loop may be close to 90° ensuring stability.

Figure 4B:
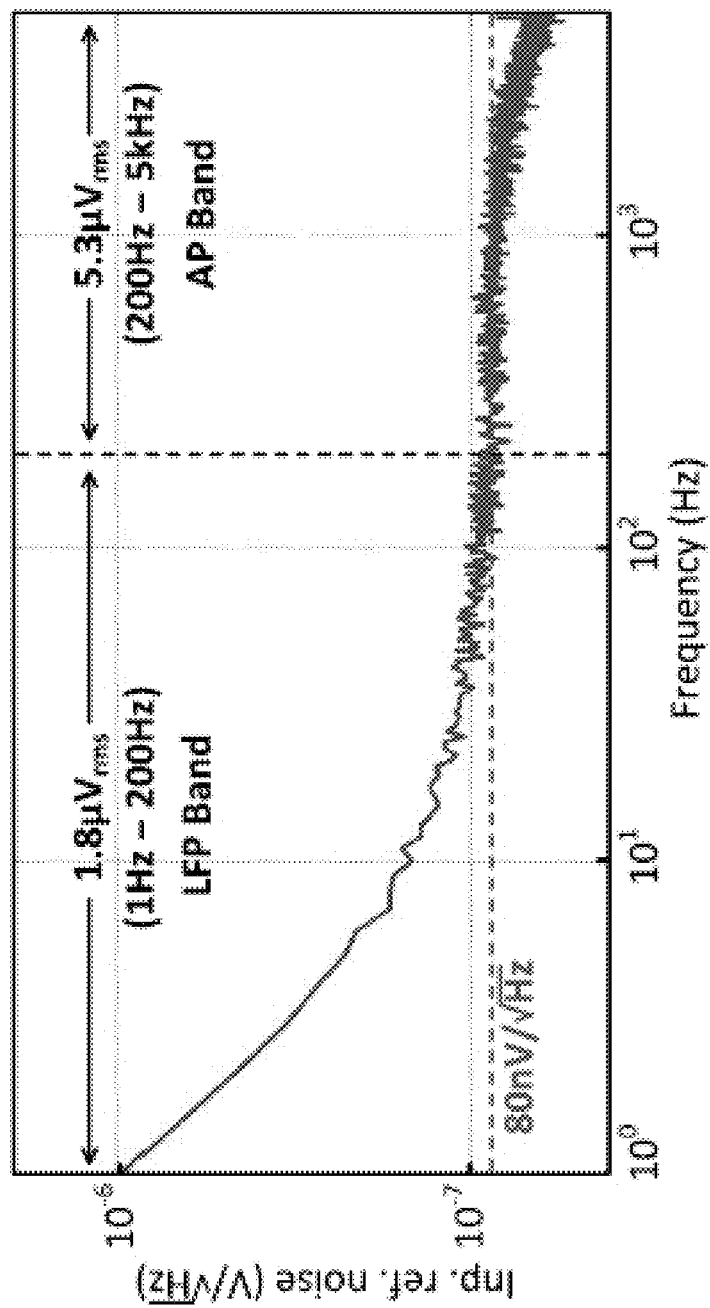
FIG. 4b illustrates measured input-referred noise of a chopper amplifier in accordance with an embodiment of the invention.
Figure 4C:
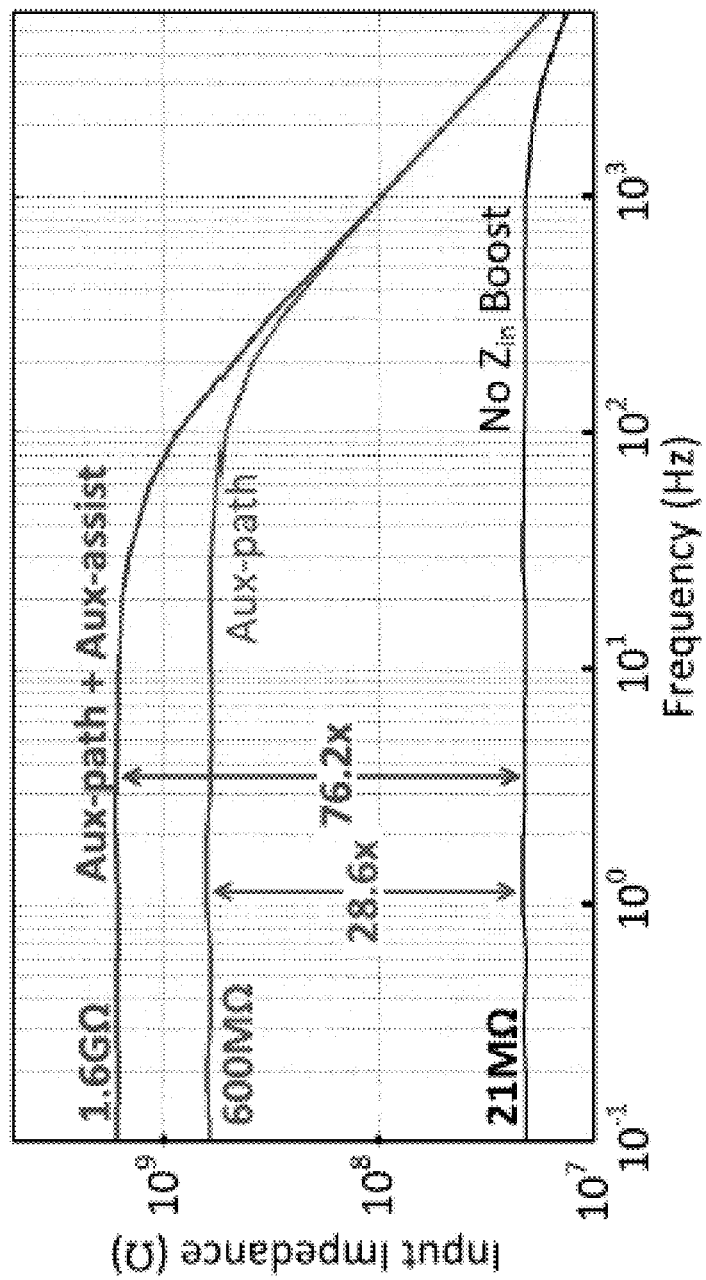
FIG. 4c illustrates measured input impedance of a chopper amplifier using different impedance boost techniques in accordance with an embodiment of the invention.

The measured input impedance of the front-end is shown in FIG. 4c. When the auxiliary path is disabled, $Z_{in}$ may be 21 MΩ. When the auxiliary path is enabled, $Z_{in}$ can be boosted to 600Ω, which can further increase to 1.6 GΩ when the auxiliary-buffer assistance is enabled. Hence $Z_{in}$ can be boosted by a factor of 76.2, with the storage capacitors $C_{aux}$ providing a 2.6× boost.

Figure 5A:
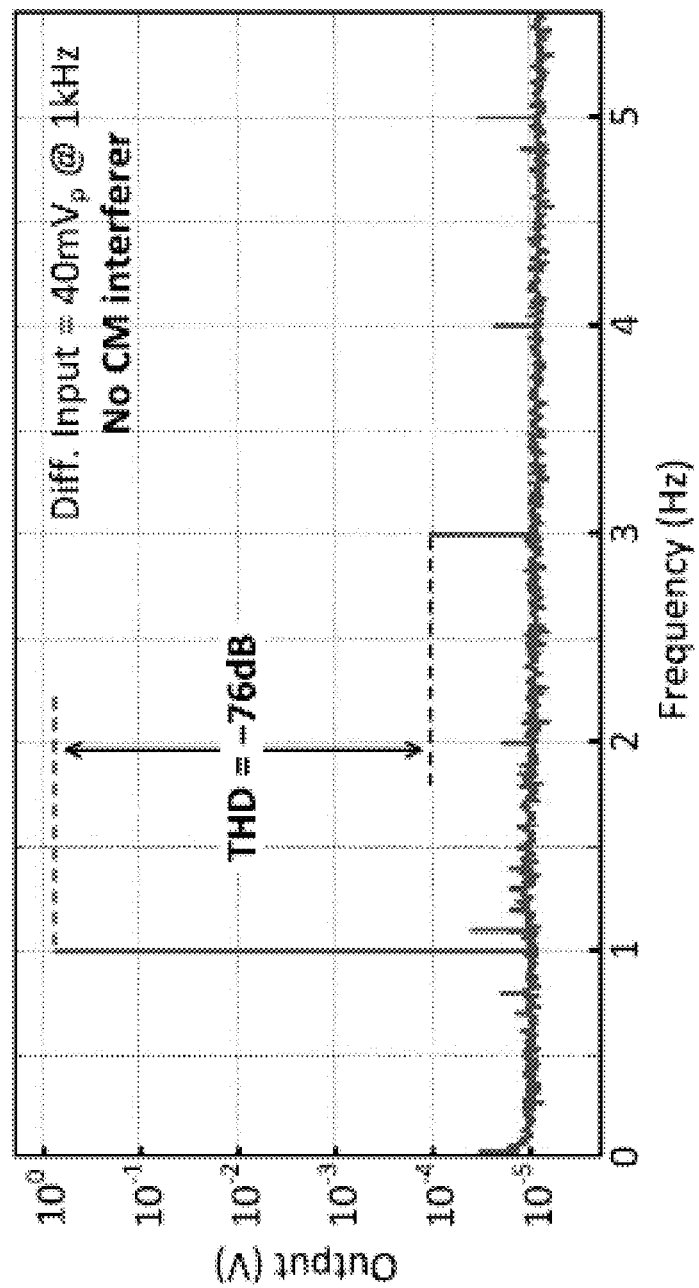
FIG. 5a illustrates measured harmonic distortion of a chopper amplifier in accordance with an embodiment of the invention.
Figure 5B:
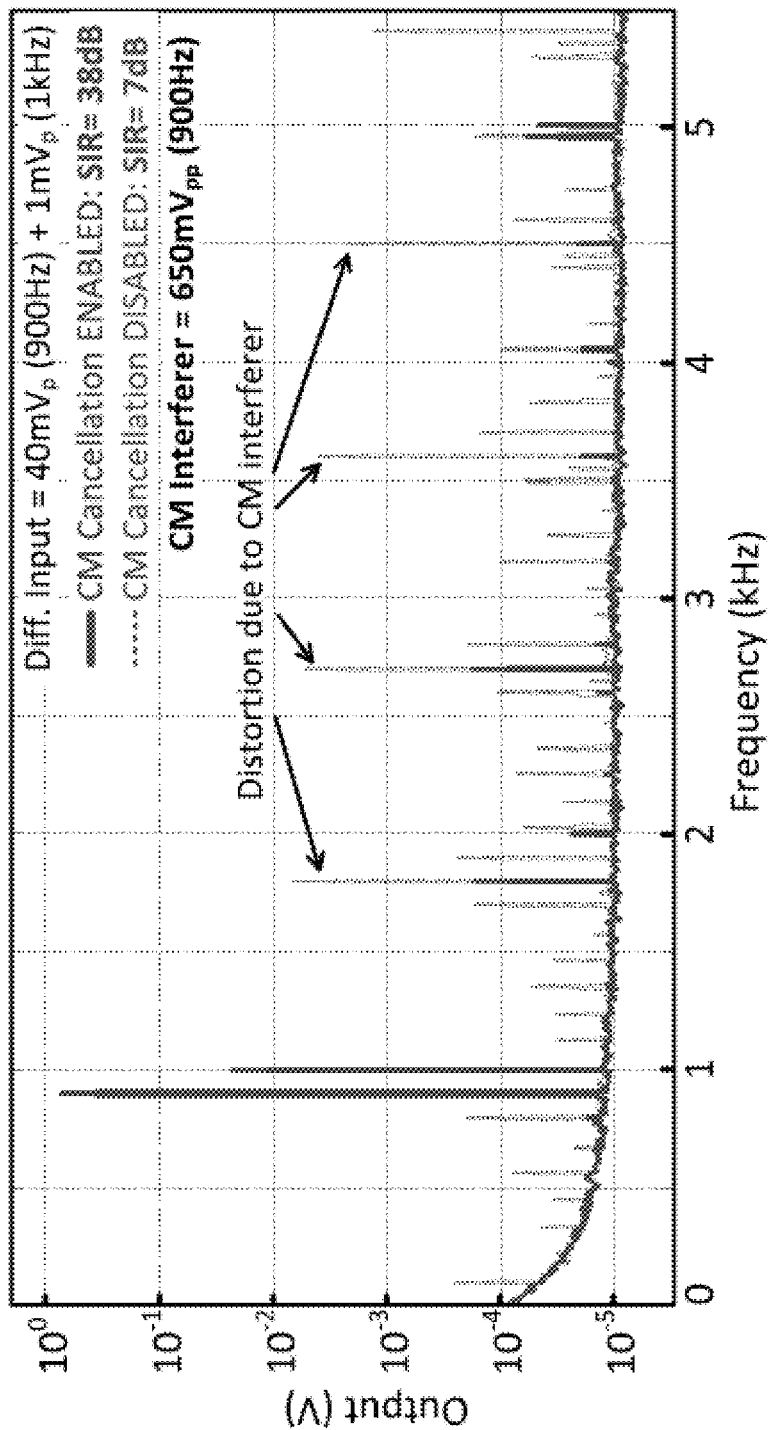
FIG. 5b illustrates response of a front-end to two-tone tests with a large CM interferer, showing the severity of distortion (without CMC), and the efficacy of the CMC path in reducing distortion with a high-frequency interferer.
Figure 5C:
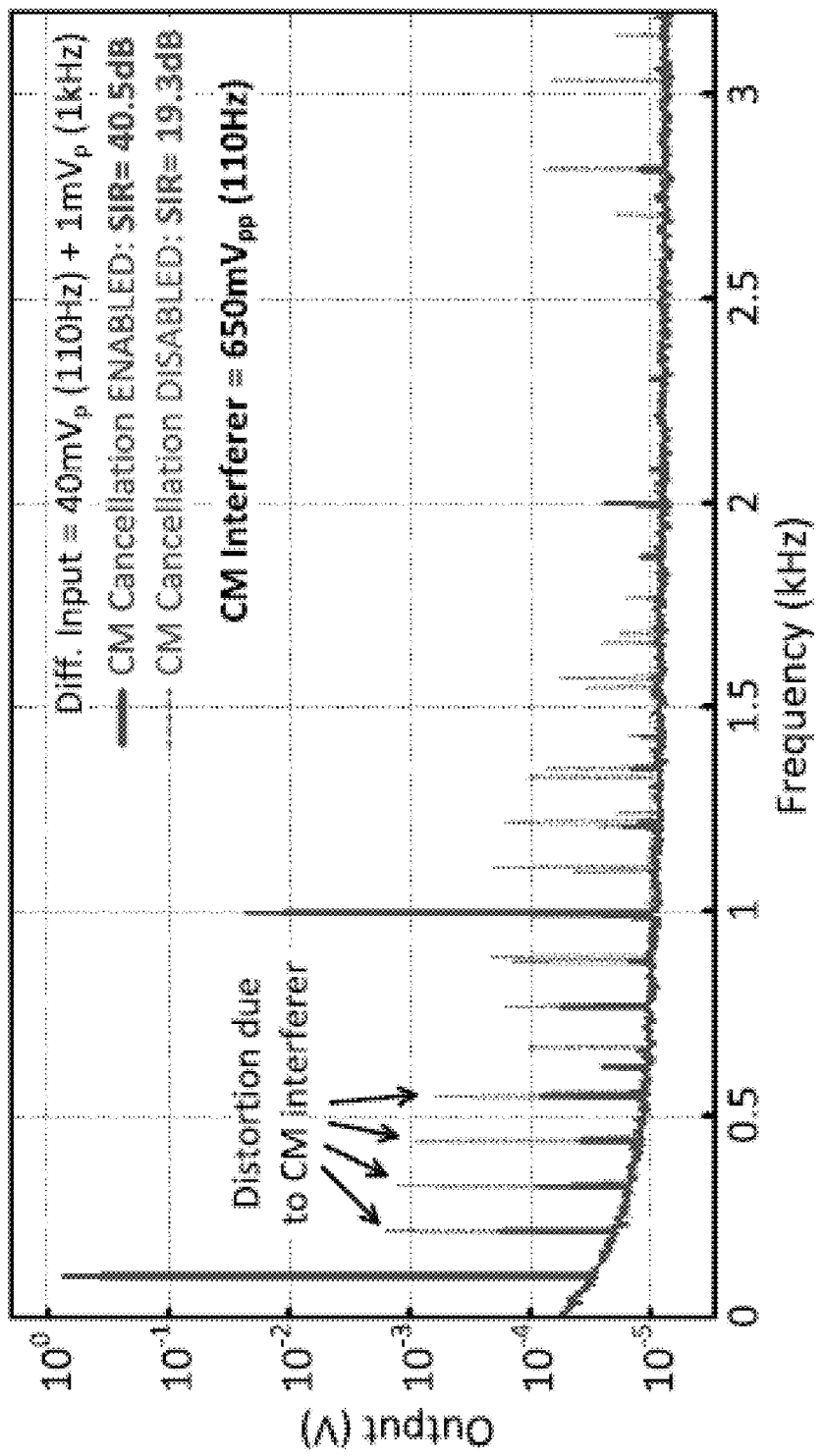
FIG. 5c illustrates response of a front-end to two-tone tests with a large CM interferer, showing the severity of distortion (without CMC), and the efficacy of the CMC path in reducing distortion with a low-frequency interferer.
Figure 12:
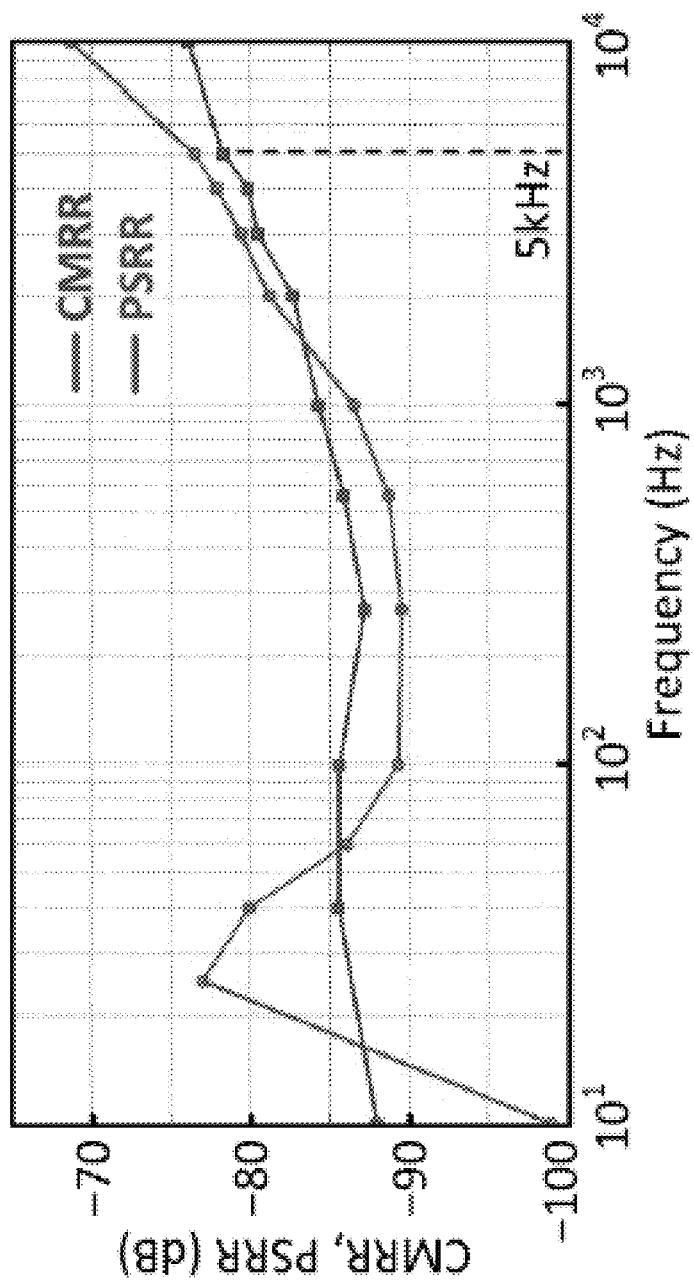
FIG. 12 illustrates common-mode rejection ratio (CMRR) and power supply rejection ration (PSRR) measurements of a complete front-end chopper amplifier in accordance with an embodiment of the invention.

The linearity measurements of a chopper amplifier in accordance with an embodiment of the invention are shown in FIG. 5a. For a differential input sinusoid of 40 m$V_p$ (or 80 m$V_{pp}$) at 1 kHz with no common-mode interferer, the measured THD was −76 dB. To measure the front-end performance in the presence of common-mode interference, two-tone tests can be performed. Realistic stimulation artifacts have significant power at multiple harmonics of the stimulation frequency due to their pulse-like nature. Hence, immunity to common-mode interference may need to be measured for frequencies up to several harmonics of the stimulation frequency. Stimulation is usually performed at frequencies below 150 Hz. Hence, performance should be measured with CM interference up to 900 Hz. A two-tone test can be conducted as follows. The differential input to the front-end can consist of the sum of a 40 m$V_p$ sinusoid at 900 Hz and a 1 m$V_p$ sinusoid at 1 kHz. A common-mode interferer of 650 m$V_{pp}$ can also be applied at 900 Hz. The 900 Hz tones represent the stimulation artifacts, while the 1 kHz tone represents the neural signal of interest. FIG. 5b shows measured results of two-tone tests in accordance with an embodiment of the invention. When the CMC path is disabled, it illustrates significant distortion components at the output. The Signal-to-Interferer ratio (SIR) can be defined as the power of the desired signal (in this case, at 1 kHz) divided by the power of the harmonics created by distortion. The SIR can be only 7 dB when the CMC path is disabled. However, when the CMC path is enabled, there is significant suppression of the distortion components and the SIR improves to 38 dB. When the CM interferer is disabled, the SIR can be 44 dB. Hence for a CM interferer of 650 $mV_{pp}$, the SIR degrades from 44 dB to 38 dB with the CMC enabled, a 6 dB drop which is assumed to be an acceptable degradation. Thus, in many embodiments, the front-end can tolerate CM interferers up to 650 $mV_{pp}$. When the frequency of the stimulation tones is lowered to 110 Hz, as illustrated in FIG. 5c, the SIR improves from 19.3 dB to 40.5 dB when the CMC path is enabled. These measurements show the efficacy of the CMC path in maintaining linearity in the presence of large CM interferers. The CMRR and PSRR can also be measured, and the results are shown in FIG. 12. The CMRR and PSRR are better than −78 dB and −76 dB respectively in the signal band (1 Hz-5 kHz).

Figure 9B:
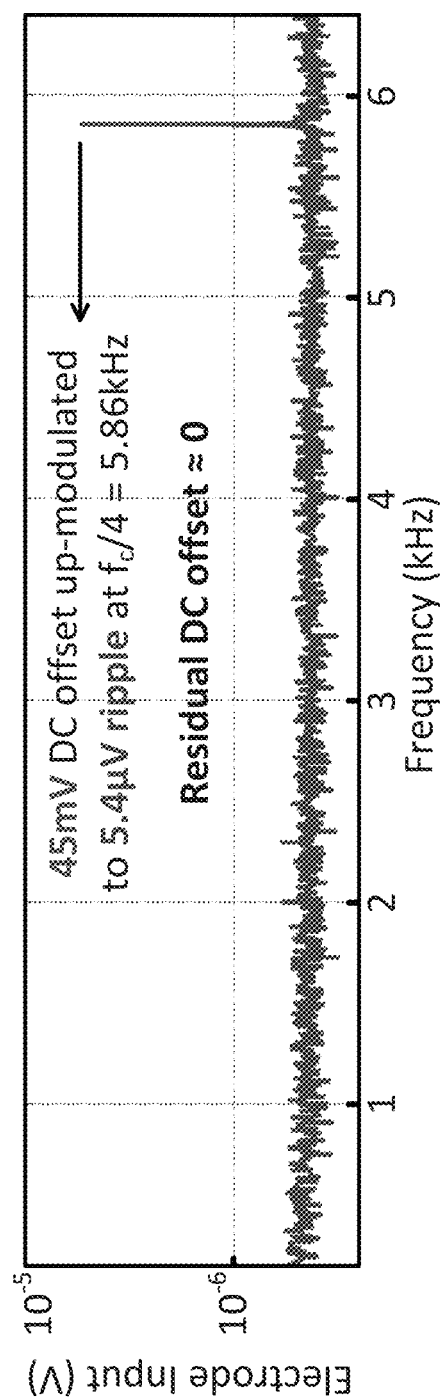
FIG. 9b illustrates measured electrode input when aux-path chopping was enabled in accordance with an embodiment of the invention.
Figure 9C:
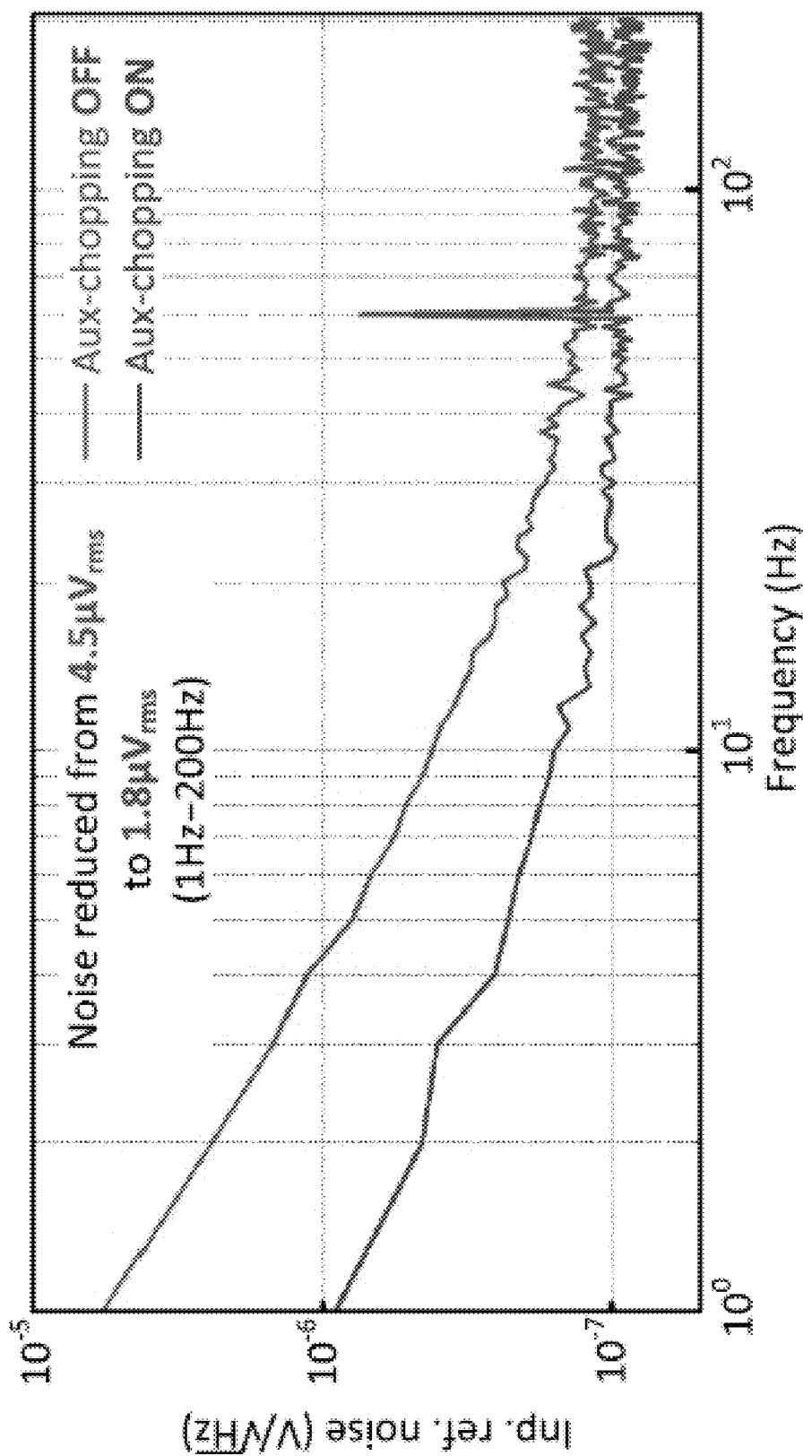
FIG. 9c illustrates measured input-referred noise showing reduced aux-buffer flicker noise when auxiliary-chopping is enabled in accordance with an embodiment of the invention.

The input-referred noise was measured to be 1.8 $\mu V_{rms}$ in the LFP band (1 Hz-200 Hz), and 5.3 $\mu V_{rms}$ in the AP band (200 Hz-5 kHz), as shown in FIG. 4b. To show the benefits of chopping in the auxiliary path, the offset appearing at the electrode was measured. When chopping in the auxiliary path, as illustrated by mixers $M_{1,2}$ in FIG. 11, was disabled, large offsets were observed at the electrode, as illustrated in FIG. 9a, and the worst-case offset was 45 mV. When the auxiliary-path chopping was enabled, the 45 mV offset reduced to zero and a 5.4 µV ripple was observed at 5.86 kHz, as illustrated in FIG. 9b. This is expected from the discussions above. The input-referred noise in the 1 Hz-200 Hz band also reduced from 4.5 $\mu V_{rms}$ to 1.8 $\mu V_{rms}$ when the auxiliary-path chopping was enabled, as illustrated in FIG. 9c.

Figure 13:
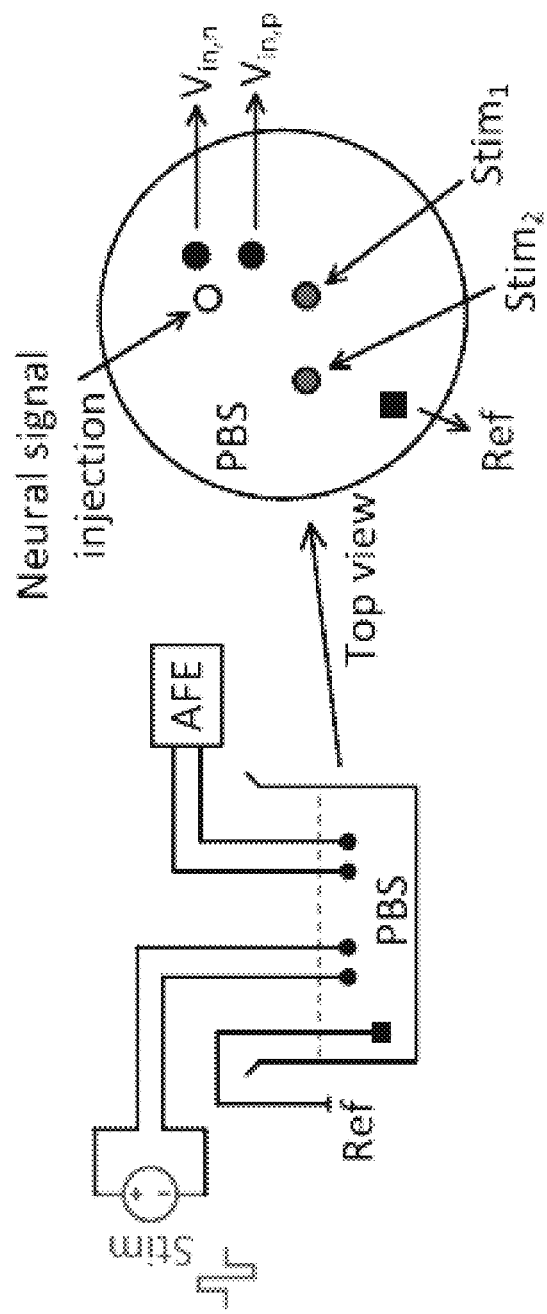
FIG. 13 illustrates a measurement setup in accordance with an embodiment of the invention.

In-vitro measurements were performed using a front-end to record signals from electrodes dipped in phosphate-buffered saline (PBS). FIG. 13 shows a measurement setup in accordance with an embodiment of the invention. A pair of electrodes ($Stim_1$ and $Stim_2$) can be used to deliver stimulation into the PBS solution, while another pair of electrodes ($V_{in,p}$ and $V_{in,n}$) can be used as sensing electrodes connected to the front-end. A separate electrode can be used to inject neural signals into the PBS solution. Although FIG. 13 illustrates a particular in-vitro measurement setup, any of a variety of in-vitro measurement setups may be utilized as appropriate to the requirements of specific applications in accordance with embodiments of the invention.

Figure 8:
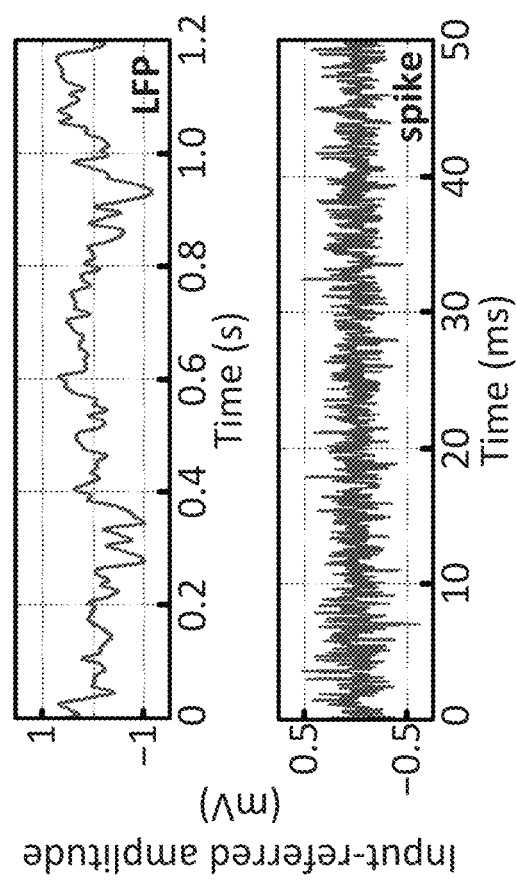
FIG. 8 illustrates in vitro measurements using pre-recorded human neural recordings (no stimulation).
Figure 14:
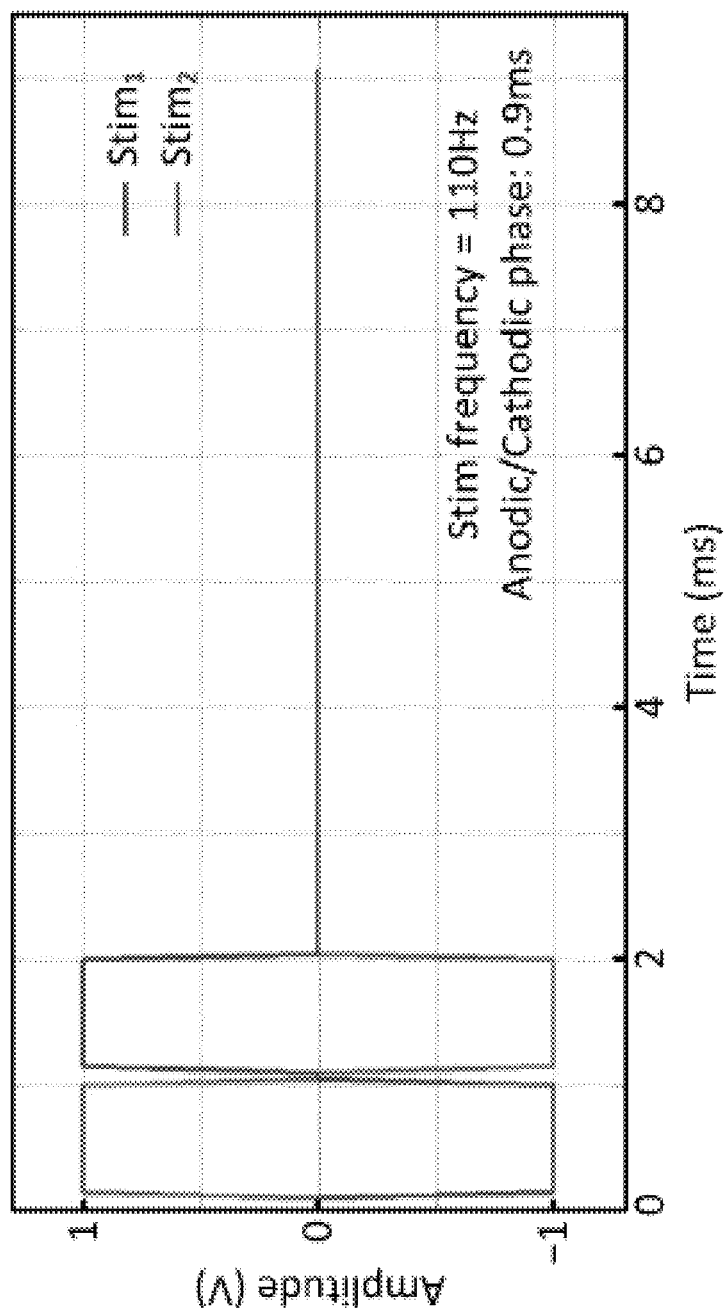
FIG. 14 illustrates stimulation waveforms used for in vitro measurements in accordance with an embodiment of the invention.
Figure 15A:
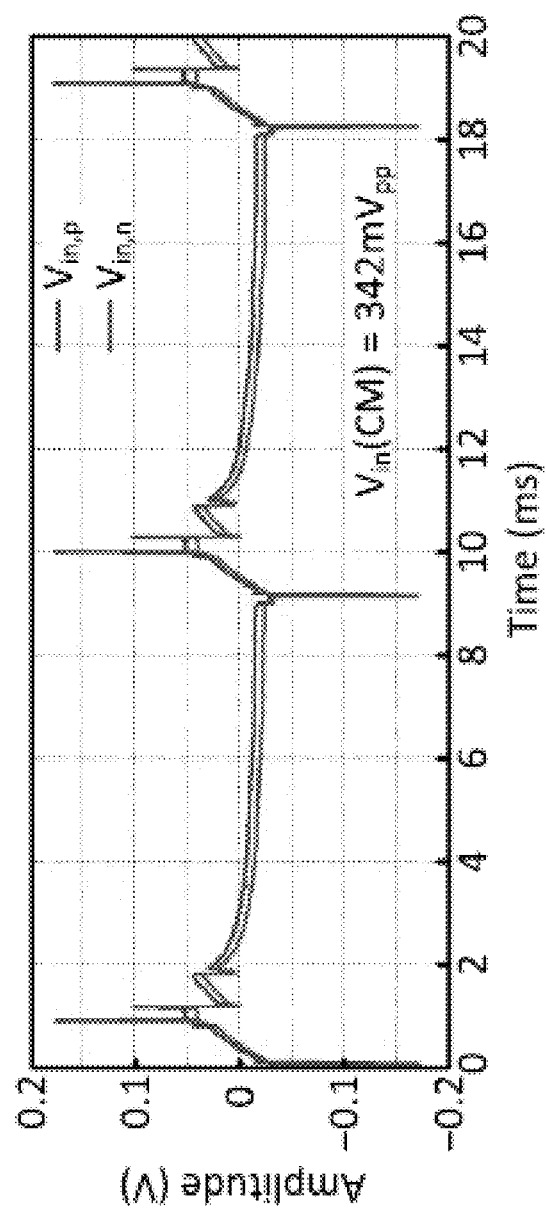
FIG. 15a illustrates measured waveforms when differential stimulation is enabled without injecting pre-recorded neural signals; recording site waveforms in accordance with an embodiment of the invention.
Figure 15B:
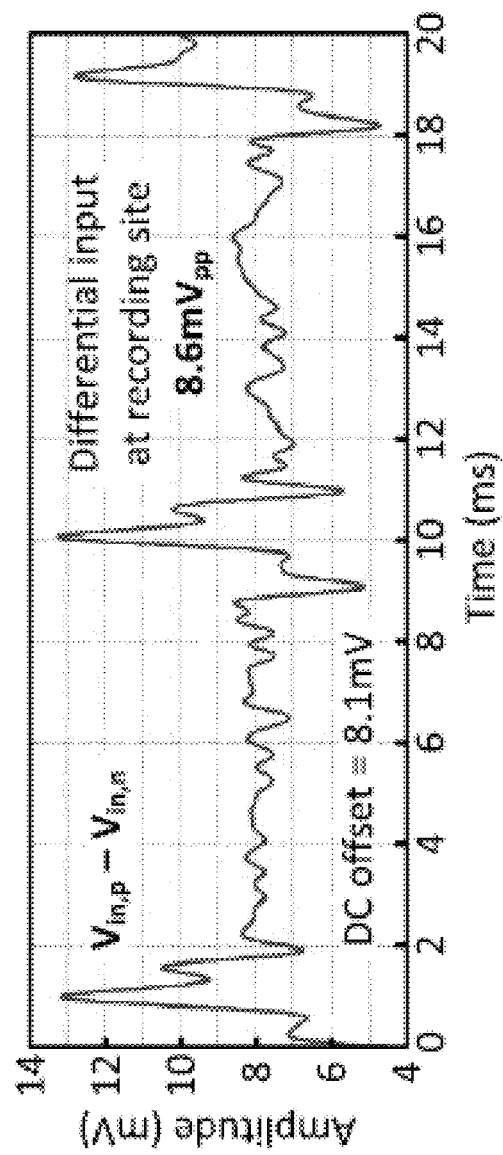
FIG. 15b illustrates measured waveforms when differential stimulation is enabled without injecting pre-recorded neural signals; differential signal at recording site in accordance with an embodiment of the invention.
Figure 15C:
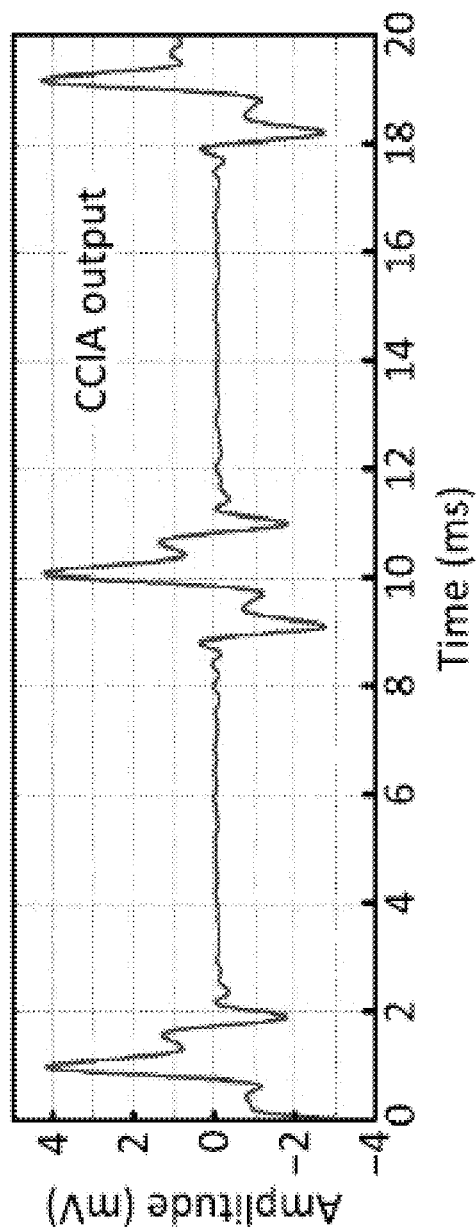
FIG. 15c illustrates measured waveforms when differential stimulation is enabled without injecting pre-recorded neural signals; measured output using CCIA (gain normalized to unity) in accordance with an embodiment of the invention.
Figure 16:
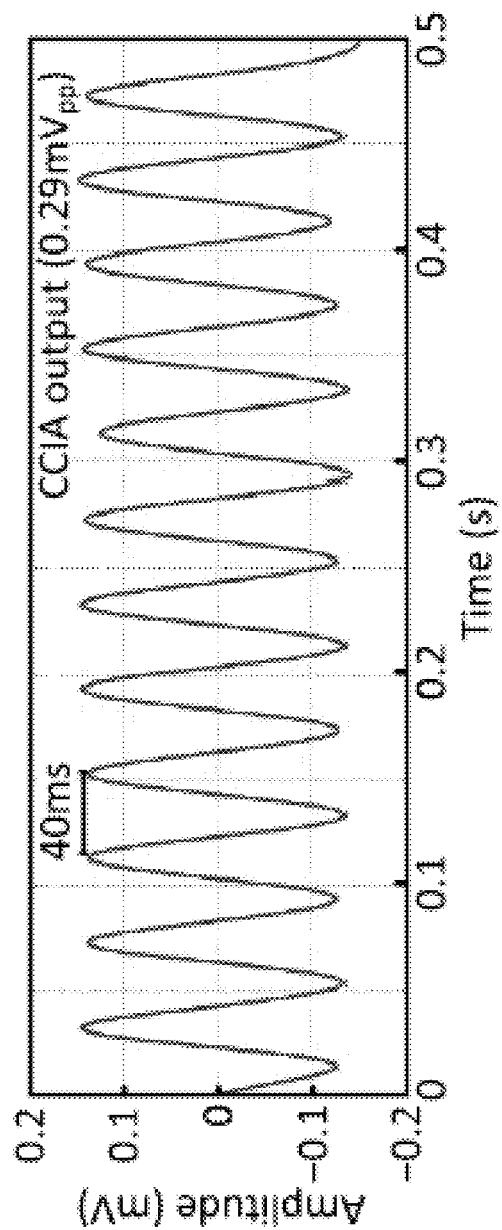
FIG. 16 illustrates measured output (LP filtered up to 50 Hz) of CCIA during stimulation; A 25-Hz sinusoid was injected to represent a neural signal in accordance with an embodiment of the invention.
Figure 17A:
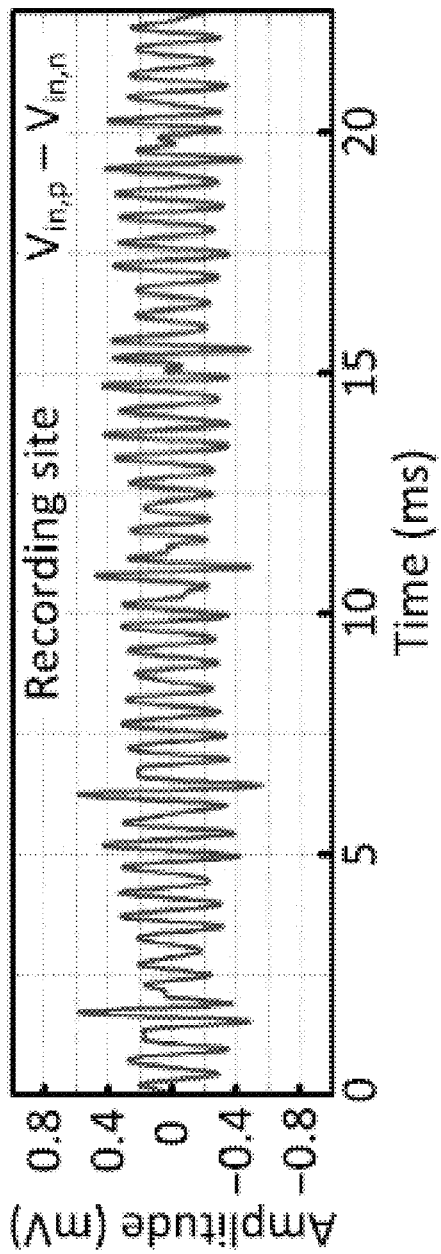
FIG. 17a illustrates measured waveforms (HP filtered from 800 Hz) during stimulation; recording site in accordance with an embodiment of the invention.
Figure 17B:
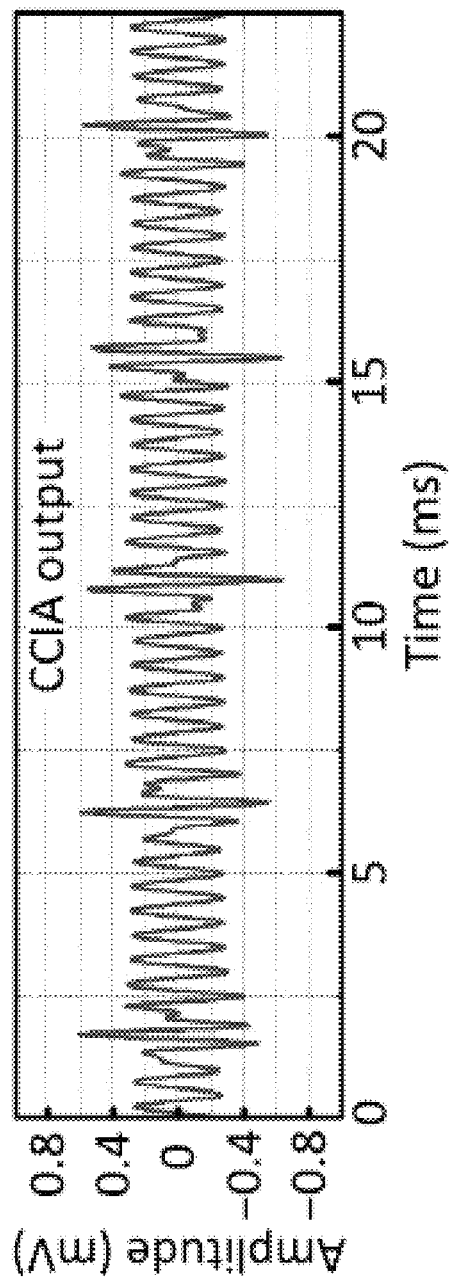
FIG. 17b illustrates measured waveforms (HP filtered from 800 Hz) during stimulation; CCIA output, a 1-kHz sinusoid was injected to represent a neural signal in accordance with an embodiment of the invention.
Figure 18A:
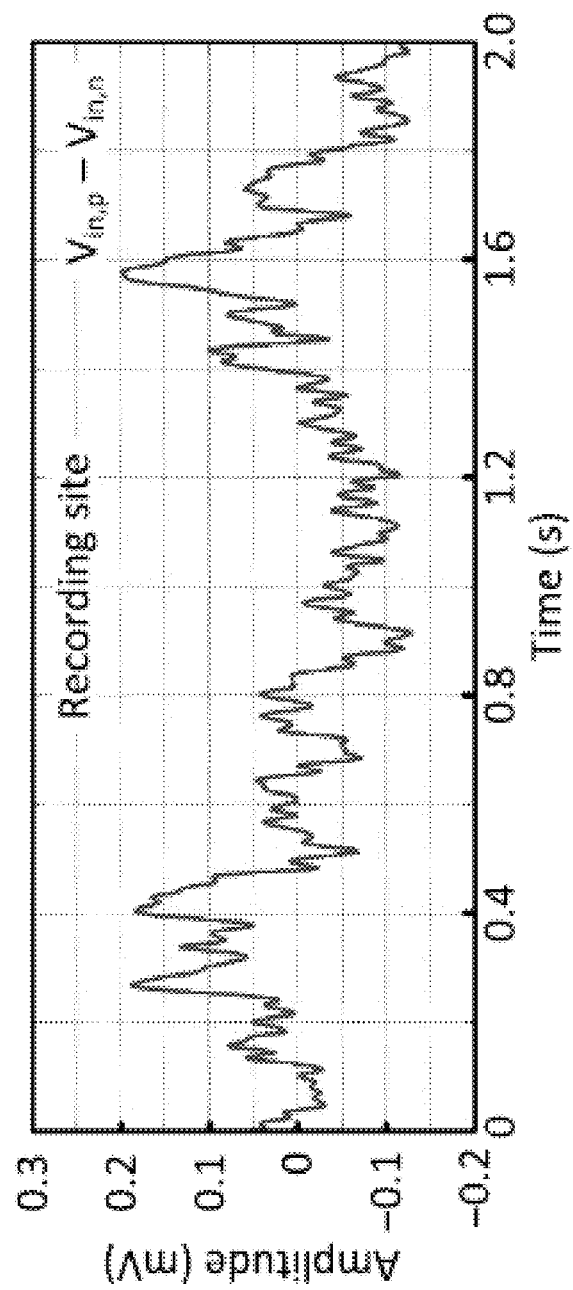
FIG. 18a illustrates measured waveforms (LP filtered up to 50 Hz) during stimulation; recoding site in accordance with an embodiment of the invention.
Figure 18B:
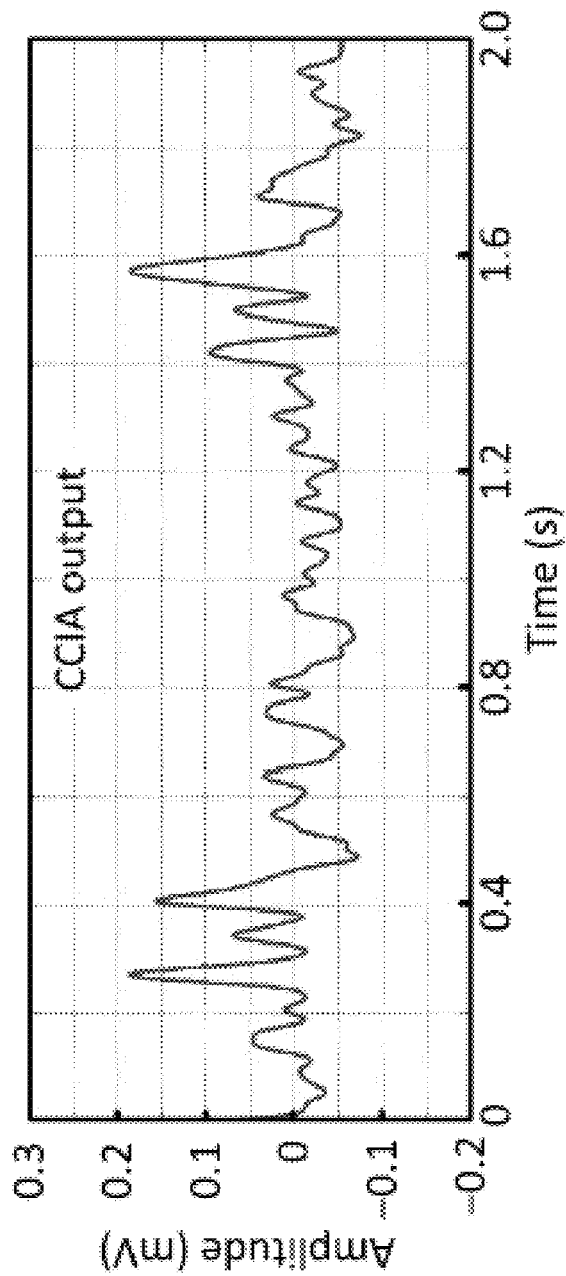
FIG. 18b illustrates measured waveforms (LP filtered up to 50 Hz) during stimulation; CCIA output, pre-recorded human neural recording were injected to emulate the neural signal in accordance with an embodiment of the invention.

FIG. 8 shows a measured output of a CCIA when pre-recorded human neural signals were injected while stimulation was disabled. To assess the magnitude of differential and common-mode artifacts due to stimulation, stimulation waveforms, as illustrated in FIG. 14, were injected into the PBS solution without neural signals, and the measured waveforms are shown in FIG. 15a through FIG. 15c. The common-mode artifact at the recording site is 342 $mV_{pp}$, as illustrated in FIG. 15a, while the differential artifact is 8.6 $mV_{pp}$, as illustrated in FIG. 15b. The measured output of the CCIA matches the differential artifact at the recording site as expected, as illustrated in FIG. 15c. Next, a 25 Hz sinusoid (representing a neural signal) was injected into the PBS solution along with the stimulation waveforms. The measured output of the CCIA, after LP filtering up to 50 Hz, shows a 25 Hz signal, as illustrated in FIG. 16. The injected sinusoid frequency was changed to 1 kHz, and the corresponding measurements, after HP filtering from 800 Hz, are shown in FIG. 17a and FIG. 17b. The differential signal at the recording site, as illustrated in FIG. 17a, matches the output of the CCIA illustrated in FIG. 17b. Since the stimulation waveform has power at the harmonics of 110 Hz, the HP-filtered outputs show residual stimulation artifacts, as illustrated by FIGS. 17a and 17b. Finally, the injected sinusoid is replaced with a pre-recorded human neural signal, and stimulation remains enabled. The measured waveforms (LP filtered up to 50 Hz) are shown in FIG. 18a and FIG. 18b. The differential signal at the recording site, as illustrated in FIG. 18a, matches the CCIA output illustrated in FIG. 18b. Hence, the proposed front-end of many embodiments is capable of recording neural signals in the presence of stimulation artifacts.

FIG. 6 compares an embodiment of the invention with the current state-of-the-art. As illustrated, may embodiments of the invention improves $Z_{in}$ by 5.3× for chopped front-ends, the linear-input range by 2×, the maximum resistance of DCRs by 32× and introduces tolerance to 650 $mV_{pp}$ common-mode interferers, while maintaining comparable power and noise performance.

Accordingly, many embodiments provide a chopper amplifier capable of closed-loop neural recording in the presence of large differential and common-mode stimulation artifacts. The assisted auxiliary path technique can enable the front-end to achieve a DC input impedance of 1.6 GΩ, and may remove a need for off-chip ac-coupling capacitors, making this front-end implantable. The linear input range can be increased to 80 $mV_{pp}$ (with THD of −76 dB) and the CMC path can introduce tolerance to 650 $mV_{pp}$ common-mode interferers. Many embodiments further introduce a Multi-rate Duty-Cycled Resistor (MDCR), which may enable realization of a much larger equivalent resistance (90 GΩ) as compared to a conventional DCR, allowing it to maintain low noise and low area. Finally, a positive feedback problem in the auxiliary path can be addressed by introducing chopping in the auxiliary path. These improvements can be made while ensuring that the front-end achieves comparable power and noise performance to the state-of-the-art. Although discussing in the context of bio-signals and/or neural signals and their respective amplifiers, the proposed systems and methods can be utilized with a variety of signals requiring amplification and thus are not limited to bio-signals, neural signals or any particular recording system.

Furthermore, although specific implementations for a high dynamic range sensing front-end are discussed above, any of a variety of implementations utilizing the above discussed techniques can be utilized for a high dynamic range sensing front-end in accordance with embodiments of the invention. While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A chopper amplifier comprising:
   a pair of inputs $V_{in,\ CM}$ configured to receive a differential input signal and a common-mode (CM) signal;
   an input capacitor $C_{in}$ connected in series with each of the pair of inputs $V_{in,\ CM}$ having capacitance $C_{in}$;

an operational amplifier $g_m$; and a common-mode cancellation (CMC) path to attenuate common-mode (CM) swings at $V_{in, CM}$, comprising:

an operational amplifier $g_{ma}$ with a gain $A_{cm}$ and capacitors $C_a$ and $C_b$ configured to sense and amplify an input CM signal; and $C_{cm}$ capacitors configured to subtract the amplified CM signal from the input signal $V_{in, CM}$ received on each of the pair of inputs.

2. The chopper amplifier of claim 1, wherein the $C_{cm}$ capacitors have capacitances that are the ratio of the capacitance of the input capacitors $C_{in}$ and the gain $A_{CM}$ of the operational amplifier.

3. The chopper amplifier of claim 1, wherein a gain in the CMC path is set by the capacitor ratio $A_{cm} = 2\, C_a/C_b$.

4. The chopper amplifier of claim 1, wherein a $C_{cm}$ capacitor is sized to be $C_{in}/A_{cm}$.

5. The chopper amplifier of claim 1, wherein capacitor $C_{in}$ and $C_{cm}$ are matching.

6. The chopper amplifier of claim 1, wherein capacitor $C_{cm}$ is sized smaller than capacitor $C_{in}$ to minimize increase in input-referred noise.

7. The chopper amplifier of claim 1, further comprising power supply circuitry configured to integrate a charge-pump on-chip to generate a local voltage supply for the operational amplifier $g_{ma}$ in the CMC path from the available voltage supply.

8. The chopper amplifier of claim 1, wherein bandwidth of the CMC path is greater than the bandwidth of the CM artifacts.

9. The chopper amplifier of claim 1, wherein the requirements of $g_{ma}$ are:

$$g_{ma}\left(\frac{C_b}{C_b + 2C_a}\right)\frac{1}{2\pi(C_b + 2C_{cm})} > 30\ \text{kHz}.$$

10. The chopper amplifier of claim 1, wherein there is no chopping at an output of the CMC path such that the CM-to-DM (differential mode) signal at the CMC output remains at baseband as compared to the up-modulated differential input signal.

11. The chopper amplifier of claim 1, further comprising at least one feedback loop including a multi-rate duty-cycled resistor (MDCR), wherein the MDCR comprises a first anti-alias filter (AAF) comprising a duty-cycled resistor (DCR) formed by $R_1$ switching at frequency $f_1$, and a capacitor $C_1$ followed by a second low-pass filter formed by a DCR $R_2$ switching at frequency $f_2$, and a capacitor $C_2$, wherein the AAF allows for a significantly reduced switching frequency $f_2$, as the AAF reduces the bandwidth of the signal flowing into the second low-pass filter.

12. The chopper amplifier of claim 11, wherein a lower limit on the switching frequency $f_2$ is determined by the bandwidth $f_{aaf}$ of the AAF and the required attenuation of the aliased components.

13. The chopper amplifier of claim 1, further comprising an auxiliary path comprising two storage capacitors with capacitance $C_{aux}$ and switching circuitry configured using offset modulation to pre-charge the input capacitors $C_{in}$ during a pre-charging phase.

14. The chopper amplifier of claim 12, further comprising passive mixers $M_{1,2}$ in the auxiliary path, where a frequency of a ripple at electrodes is equal to the clock frequency $F_{aux}$ used in the mixers $M_{1,2}$.

* * * * *